United States Patent [19]
Vyas et al.

[11] Patent Number: 5,700,820
[45] Date of Patent: Dec. 23, 1997

[54] POLYMORPHIC FORMS OF TROGLITAZONE HAVING ENHANCED ANTI-DIABETIC ACTIVITY AND A PROCESS FOR THEIR PREPARATION

[75] Inventors: Krishnamurthi Vyas; Chebiyyam Prabhakar; Sreenivas Dharmaraja Rao; Mamillapalli Ramabadhra Sarma; Om Gaddam Reddy; Rajagopalan Ramanujam; Ranjan Chakrabarti, all of Andhra Pradesh, India

[73] Assignee: Dr. Reddy's Research Foundation, Hyderabad, India

[21] Appl. No.: 665,867

[22] Filed: Jun. 19, 1996

[30] Foreign Application Priority Data

Feb. 20, 1996 [IN] India ............... 276/MAS/96

[51] Int. Cl.$^6$ .............. C07D 417/12; A61K 31/425
[52] U.S. Cl. ............. 514/369; 514/370; 548/183; 548/184; 548/191
[58] Field of Search ............... 514/369, 370; 548/183, 184, 191

[56] References Cited

U.S. PATENT DOCUMENTS

| | | | |
|---|---|---|---|
| 4,316,849 | 2/1982 | Bonaldi et al. | 260/397.1 |
| 4,572,912 | 2/1986 | Yoshioka et al. | 514/369 |
| 5,248,699 | 9/1993 | Sysko et al. | 514/647 |
| 5,319,097 | 6/1994 | Holohan et al. | 548/507 |

FOREIGN PATENT DOCUMENTS

| | | |
|---|---|---|
| 3255984 | 3/1988 | Australia . |
| 0014590 | 8/1980 | European Pat. Off. . |
| 0022527 | 1/1981 | European Pat. Off. . |
| 0490648 | 6/1992 | European Pat. Off. . |

OTHER PUBLICATIONS

Horikoshi, H. et al. Annul. Rep. Sankyo Res. Lab. 46, 1–57 (1994).

*Primary Examiner*—Frederick Krass
*Attorney, Agent, or Firm*—Ladas & Parry

[57] ABSTRACT

Novel polymorphic forms of Troglitazone and methods for preparing the polymorphic forms of Troglitazone. The polymorphic forms of Troglitazone can be used to treat diabetic ailments.

21 Claims, 26 Drawing Sheets

POLYMORPHIC FORMS OF TROGLITAZONE HAVING ENHANCED ANTI-DIABETIC ACTIVITY AND A PROCESS FOR THEIR PREPARATION

BACKGROUND OF THE INVENTION

This invention relates to a discovery of the preparation of novel polymorphic/pseudopolymorphic forms of Troglitazone and process for the preparation of various polymorphic/pseudopolymorphic forms of Troglitazone. Troglitazone is 5-[[4-[3(3,4- dihydro-6-hydroxy-2, 5, 7, 8-tetramethyl-2H-1-benzopyran-2-yl) methoxy] phenyl] methyl] 2, 4-thiazolidinedione, having the formula I shown below. The polymorphic forms prepared by the process of the present invention are more active, as an antidiabetic agent, than the hitherto known Troglitazone.

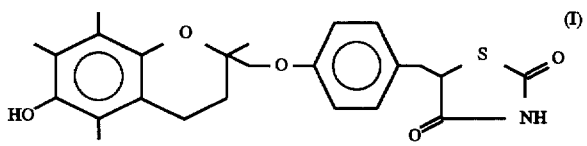

Out of the many drugs available for the treatment of diabetic ailments, the thiazolidinedione derivatives are very prominent and are considered as much superior effective-constituents compared to the sulphonyl ureas. Troglitazone, one such thiazolidinedione, which exhibited euglycemic effect, was reported in the year 1983 by Sankyo Co. Ltd., Japan (Japanese Patent No. 60-051189/Australian Patent No. 570067) and created interest in the field, ever since.

Previously, the oral diabetic medicines consisting of sulphonyl urea were believed to be effective in bringing down the sugar level in blood (Hypoglycemic) but they lacked efficiency in preventing/reducing diabetes related complications like cataract, nervous break down, retinopathia etc. (which are usually the chronic ailments accompanied by diabetes). Aldose reductase is the enzyme which reduces aldose present in the humans and animals into corresponding polyols which, in turn, are stored or accumulated in the kidneys, peripheral nerves, eye lens of the diabetic patients and manifest themselves in the above mentioned complications.

With a view to prevent/cure the chronic complications of diabetes, research is being conducted round the world in recent times. Troglitazone hitherto known is being considered today as one of the most effective antidiabetic drugs which has a multipurpose activity not only acting on diabetes itself but also on the reduction of the triglycerides and also on the accompanying complications mentioned above. Indeed, the said Troglitazone is emerging as the first drug candidate of englycemic class of antidiabetic agents.

The latest trend that has, of late, crept into the pharmaceutical industry is the studies on polymorphism in drugs and the difference in the activity of different polymorphic forms of a given drug. By the term polymorphism we mean to include different physical forms, crystal forms, crystalline/liquid crystalline/non-crystalline (amorphous) forms. This has especially become very interesting after observing that many antibiotics, antibacterials, tranquilizers etc., exhibit polymorphism and some/one of the polymorphic forms of a given drag exhibit superior bio-availability and consequently show much higher activity compared to other polymorphs. Sertraline, Frentizole, Ranitidine, Sulfathiazole, Indomethacine etc. are some of the important examples of pharmaceuticals which exhibit polymorphism.

SUMMARY OF THE INVENTION

Sankyo Co. Ltd., Japan states in its annual report (Annu. Rep. Sankyo. Res. lab., 46, pp. 1–57, 1994) that the relative configurations of the diastereomers have been determined by X-ray crystallographic analysis and that the crystal and molecular structure of troglitazone is under preparation. The report does not touch upon the possibility/observation that troglitazone exists in different polymorphic forms. There is no published literature regarding such an observation till date. Polymorphism in drugs is a topic of current interest and is evident from the host of patents being granted. To cite a few, U.S. Pat. No. 5,248,699 discusses about five polymorphic forms of Sertraline hydrochloride while EP 014590 describes four polymorphic forms of Frentizole. EP 490648 and EP 022527 also deal with the subject of polymorphism in drugs. The fact that polymorphism in troglitazone has not been studied earlier coupled with the current interest in the field of polymorphism in drugs prompted us to take up this investigation. Our observations and results form the subject matter of the present invention.

We have, due to our sustained research directed towards finding out effective antidiabetic drugs, observed that Troglitazone can be prepared in different polymorphic forms possessing anti-diabetic activity. We have, in the course of research, prepared and studied at least six polymorphic forms of Troglitazone. These polymorphs have been designated, by us, as Forms 1,2,3,4,5 & 6.

Our present invention relates to an observation that Troglitazone exhibits polymorphism, which has not been reported till date. Polymorphic Forms 1,2,3 and 6 are obtained by different modes of recrystallization while the polymorphic Forms 4 and 5 are derived from melting/heating any of the polymorphic Forms 1, 2, 3 and 6. A slow recrystallization of the crude Troglitazone gives the polymorphic Form-1. On the other hand, a fast recrystallization of the same crude Troglitazone gives the polymorphic Form-2. This Form-2 of 99% High Pressure Liquid Chromatography (HPLC) purity upon slow recrystallization gives the polymorphic Form-3. Polymorphic Forms 1, 2, 3 and 6 when melted, produce a glossy/transparent material which on thorough grinding gives a fine powder. This pale yellow powder does not give any peaks due to X-Ray Diffraction (XRD). This could be amorphous/liquid crystalline in nature. This amorphous/liquid crystalline form is designated as Form-4. Interestingly, the non-crystaline Form-4 on isothermal heating at 130° C. yields the crystaline form, designated as Form-5.

All these polymorphic forms were proved to be identical in solution as evident from Nuclear Magnetic Resonance (NMR), Ultra Violet (UV) & Mass spectral data. On the other hand, solid state techniques like Differential Scanning Calorimetry (DSC), Powder X-Ray Diffractometry (XRD) and Infra Red spectroscopy (IR) revealed the difference among these forms.

DSC of the polymorphic Form-1 and polymorphic Form-3 have one melting endotherm each at ~180° C. and ~186° C. (FIGS. 1 & 2) respectively. Polymorphic Form-2 exhibits an endotherm, in the temperature region 110°–120° C. (hereafter referred as Peak 1) before the melting endotherm in the region 165°–190° C. as shown in FIG. 3. It was also observed that when the polymorphic Form-2 is heated to 150° C. and cooled, the rerecorded DSC thermogram showed the reduction and absence of the peak 1 as represented by FIGS. 4 & 5 respectively, indicating the conversion of the polymorphic Form-2 into another polymorphic form completely/partially. It was confirmed by Thermo Gravimetry (TG)—Mass spectroscopic studies that the Peak 1 present in polymorphic Form-2 is not due to any volatile material as there was no weight loss in TG and no mass was detected by analyzing the evolved gases from TG, using mass spectrometry. However, the possibility of mixture of polymorphs constituting this polymorphic Form-2 can not be ruled out. Interestingly, DSC studies on polymorphic Form-4 exhibited (FIG. 6) a small endotherm at ~57° C., an exotherm at ~100°–130° C. and a melting endotherm at ~177° C. The endotherm at ~57° C. could be because of phase transition/loss of some volatile material. The exotherm at ~100°–130° C. is due to crystallization while the endotherm at ~177° C. is due to melting. Hence, in principle, if the amorphous/liquid crystalline polymorphic Form-4 when heated at ~130° C., should result in a crystalline form. It is reasonable to expect the amorphous/liquid crystalline polymorphic Form-4 to acquire crystallinity when heated at ~130° C. Indeed, when the polymorphic Form-4 was heated at 130° C., it attained crystallinity and the DSC of this material exhibited only the melting endotherm (FIG. 7) at ~177° C., indicating the absence of phase transition and the disappearance of liquid crystalline nature. The new crystalline form thus obtained is designated as polymorphic Form-5. The DSC study also reveals that the polymorphic Form-4 is not only noncrystalline/liquid crystalline but also metastable in nature. The plausible reason for the enhanced activity of the polymorphic Form-4 may be due to the thermodynamically less stable nature of noncrystalline/liquid crystalline form. The polymorphic Form-6 exhibits a single melting endotherm at ~105° C. (FIG. 8)

The XRD of the crystalline polymorphic Forms 1,2,3,5 & 6 were formed to be different from each other (FIGS. 9–13) while the polymorphic Form-4 showed no XRD pattern confirming its amorphous/liquid crystalline nature as shown in the (FIG. 14). FIG. 15 gives the powder X-ray diffraction pattern of the Forms 1, 2, 3, 5 and 6 to facilitate easy comparison.

The Infrared absorption spectra of Forms 1 to 6 in potassium bromide are different from one another which become apparent only after closer examination. The spectra are depicted in FIGS. 16–21 respectively. The overlapped IR spectra of all the Forms 1 –6 (FIG. 22) and the sectional expansions (FIGS. 23–26) are also provided. A qualitative comparison of such spectra (FIGS. 22–26) reveals the following differences.

a. Forms 2 & 6 exhibit absorption bands of medium intensity at ~3650 $cm^{-1}$ while no absorption is observed for the others (FIG. 23).

b. Form 1 exhibits a strong absorption with a shoulder at ~3450 $cm^{-1}$ while Forms 3 & 5 absorb without a shoulder. On the other hand Form 2 exhibits a band at ~3550 $cm^{-1}$, while Form 4 has it at ~3500 $cm^{-1}$ (FIG. 23).

c. Forms 1 & 2 have a weak absorption at ~3300 $cm^{-1}$, Form 3 has a strong band while no absorption for the rest (FIG. 23).

d. Forms 1 & 3 have a strong absorption at ~2980 $cm^{-1}$ with a shoulder at ~2925 $cm^{-1}$, while Forms 2, 4 and 5 show only a weak peak at ~2980 $cm^{-1}$ with no shoulder. Form 6 shows no absorption in this region (FIG. 23).

e. All the forms show absorption ~1750 $cm^{-1}$ and ~1700 $cm^{-1}$. Only Form 5 shows a shoulder in both these wavenumbers while Form 1 has a shoulder in the latter (FIG. 24).

f. Forms 2 & 6 have a strong peak at ~1255 $cm^{-1}$, while the rest have it at ~1240 $cm^{-1}$ (FIG. 25).

g. Form 3 has a weak absorption at ~700 $cm^{-1}$ while others have no absorption. (FIG. 26).

h. Form 6 exhibits three weak absorption bands while the others have negligible absorption (FIG. 26).

DETAILED DESCRIPTION OF THE INVENTION

Figure 1:
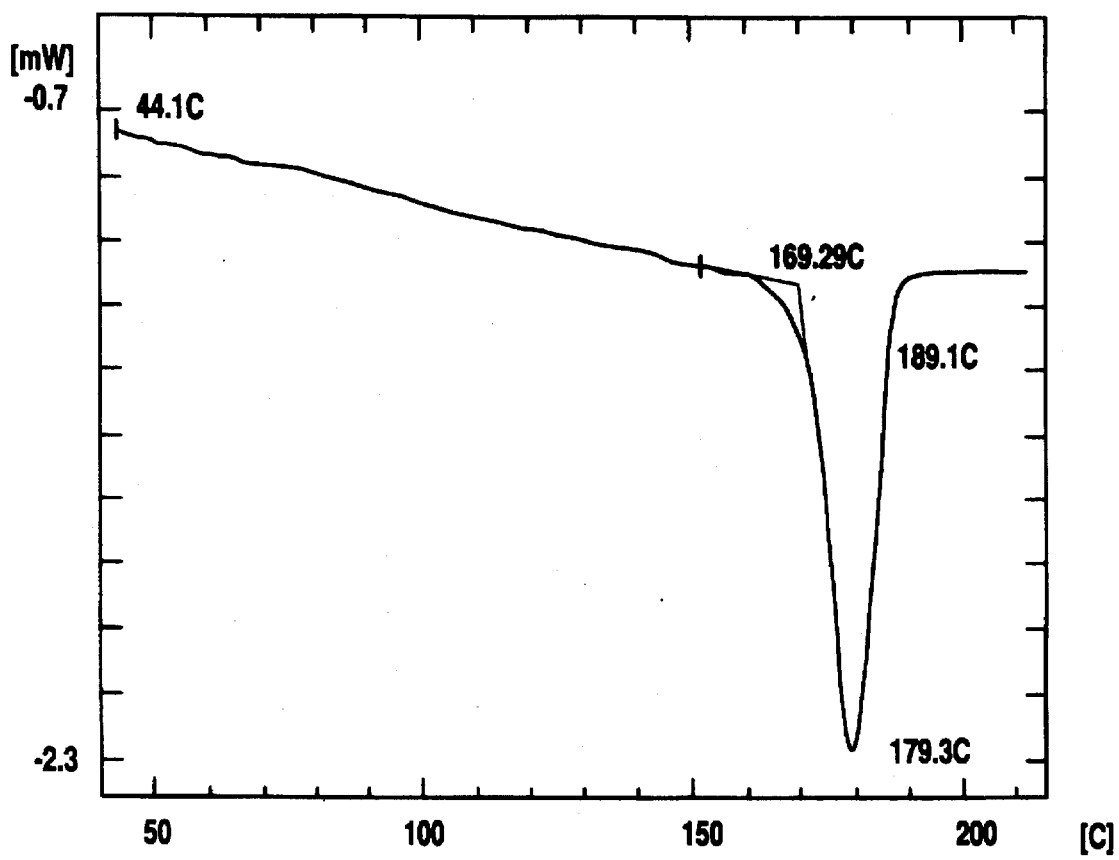
FIG. 1 is a characteristic differential scanning calorimetric thermogram of Form 1.

Accordingly, the present invention provides a process for the preparation of novel polymorphic Form-1 of Troglitazone having the formula I shown in the drawing accompanying this specification which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent and (iv) cooling the resulting solution slowly to room temperature at a rate of 0.1° to 1° C./minute over a period in the range of 24–72 h to produce the polymorphic Form-1 of Troglitazone which is characterized by the following data.

DSC: Endotherm at 179.3° C. (onset at 169.3° C.) (FIG. 1)

Figure 9:
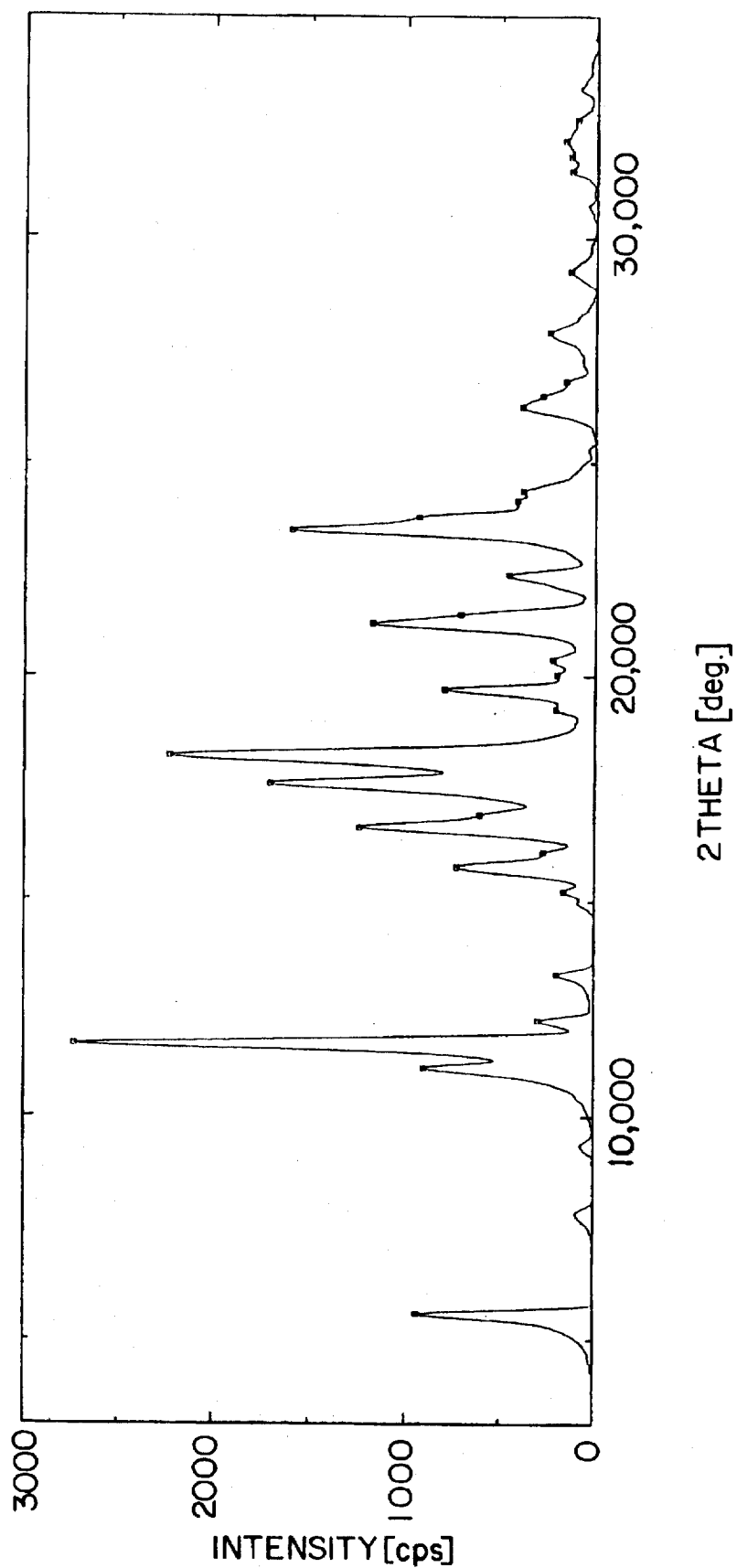
FIG. 9 is a characteristic X-ray powder diffraction pattern of Form 1.

X-ray powder diffraction (2θ): 5.56, 11.10, 11.66, 15.72, 16.62, 17.62, 18.24, 19.70, 21.20, 21.42, 22.32, 23.40, 23.70, 24.06, 24.36, 26.26 (FIG. 9)

Figure 16:
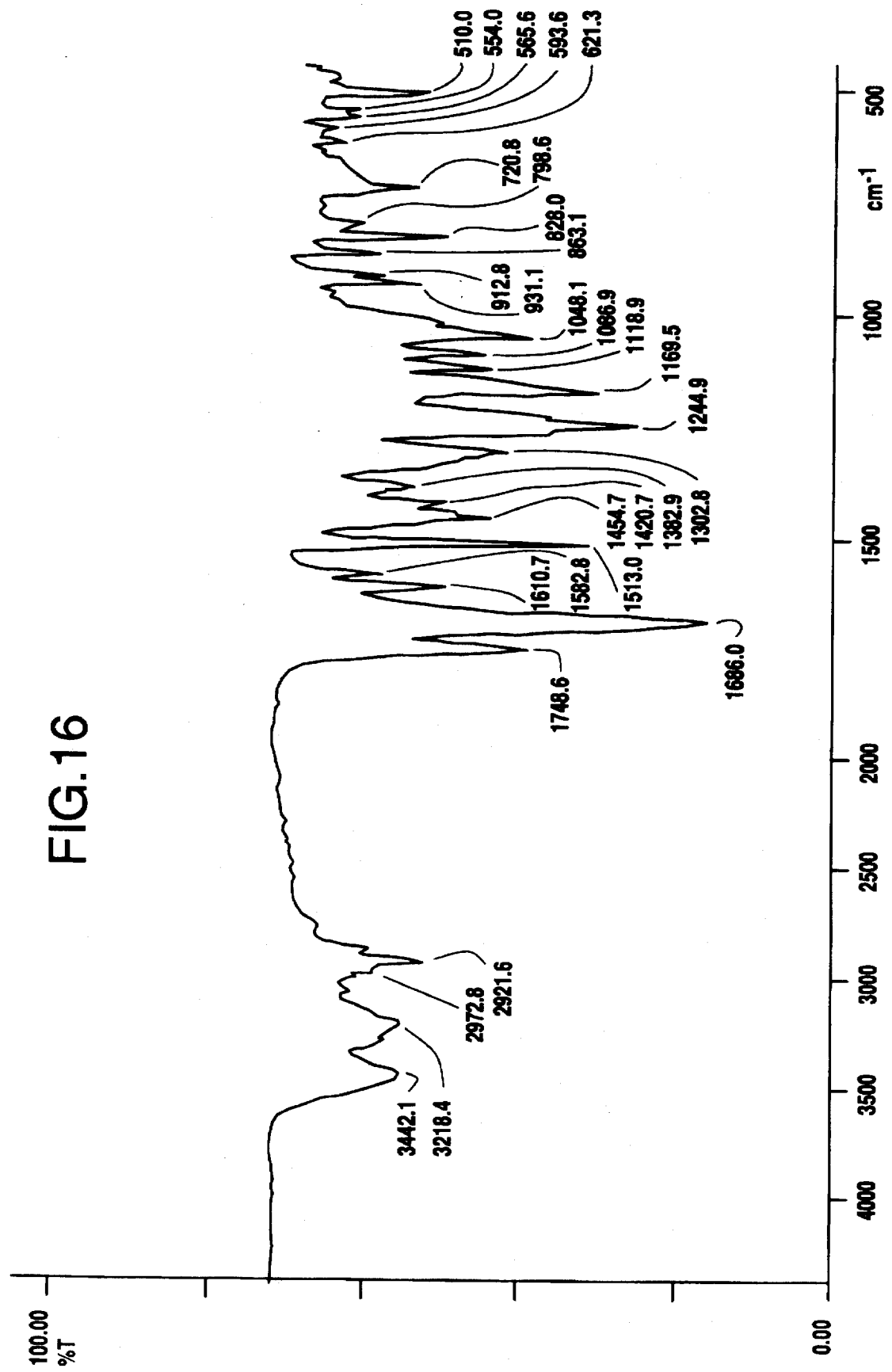
FIG. 16 is a characteristic infrared absorption spectrum of Form 1 in potassium bromide (KBr).

Infrared absorption bands (cm$^{-1}$): 3442(w), 3218(w), 2921(w), 1748(m), 1686(s), 1610(w), 1582(w), 1513 (s), 1454(w), 1420(w), 1382(w), 1302(m), 1244(s), 1169(m), 1118(w), 1086(w), 1048(m), 931(w), 863 (w), 827(w), 798(w), 720(w), 509(w). (FIG. 16)

w=weak, m=medium, s=strong

According to another feature of the invention, there is provided a process for the preparation of novel polymorphic Form-2 of Troglitazone having the formula I which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent and (iv) scratching the resulting solution, while cooling rapidly to a temperature between 0° to −20° C. at a rate of 2° to 10° C./minute over a period in the range of 10–30 min. to precipitate the polymorphic Form-2 of Troglitazone which is characterized by the following data.

Figure 3:
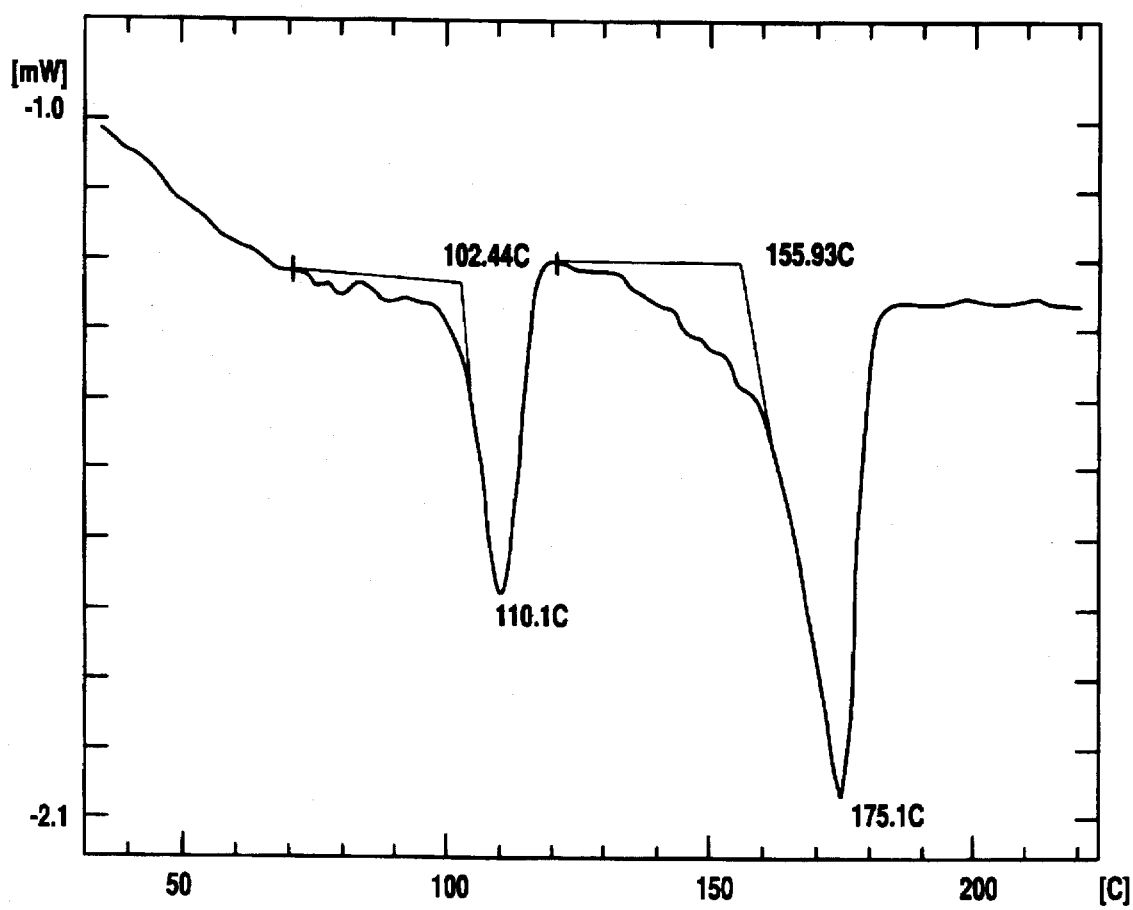
FIG. 3 is a characteristic differential scanning calorimetric thermogram of Form 2.
Figure 4:
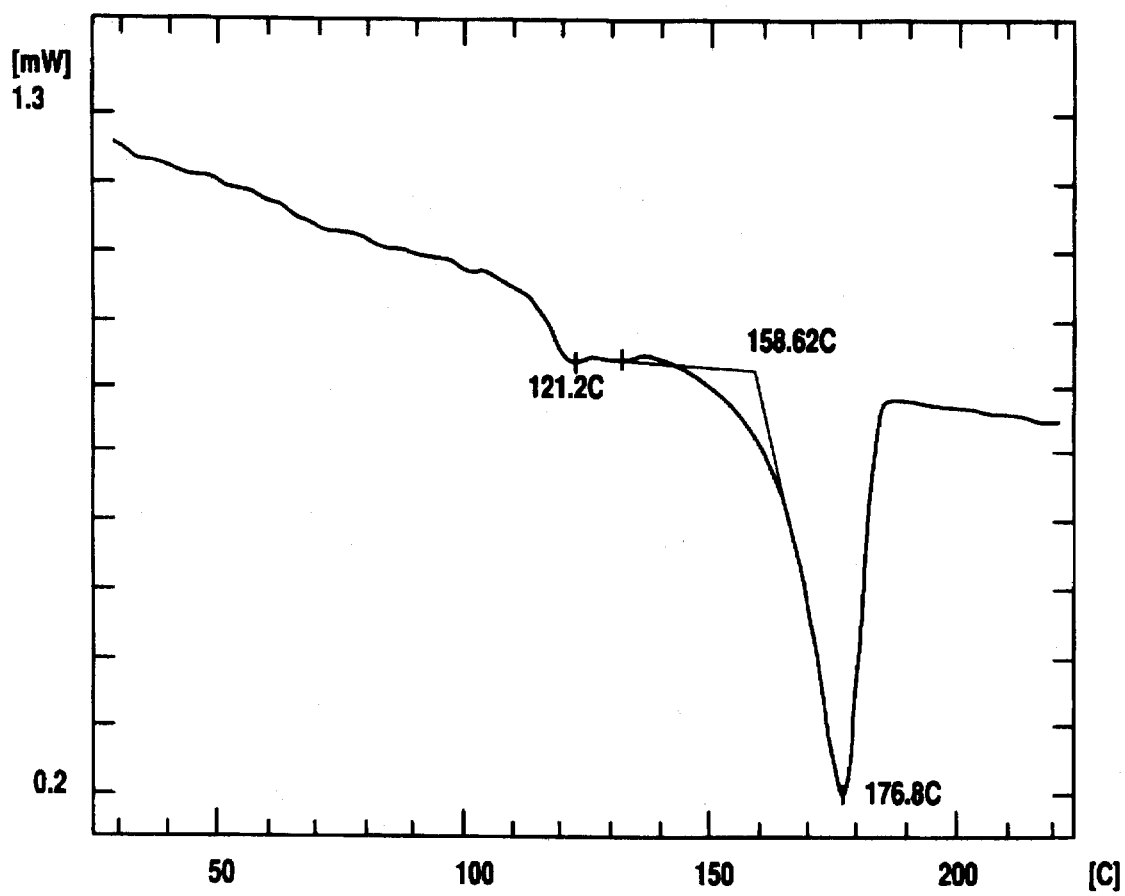
FIG. 4 is a characteristic differential scanning calorimetric thermogram of Form 2 showing the reduction of peak 1 after heating.
Figure 5:
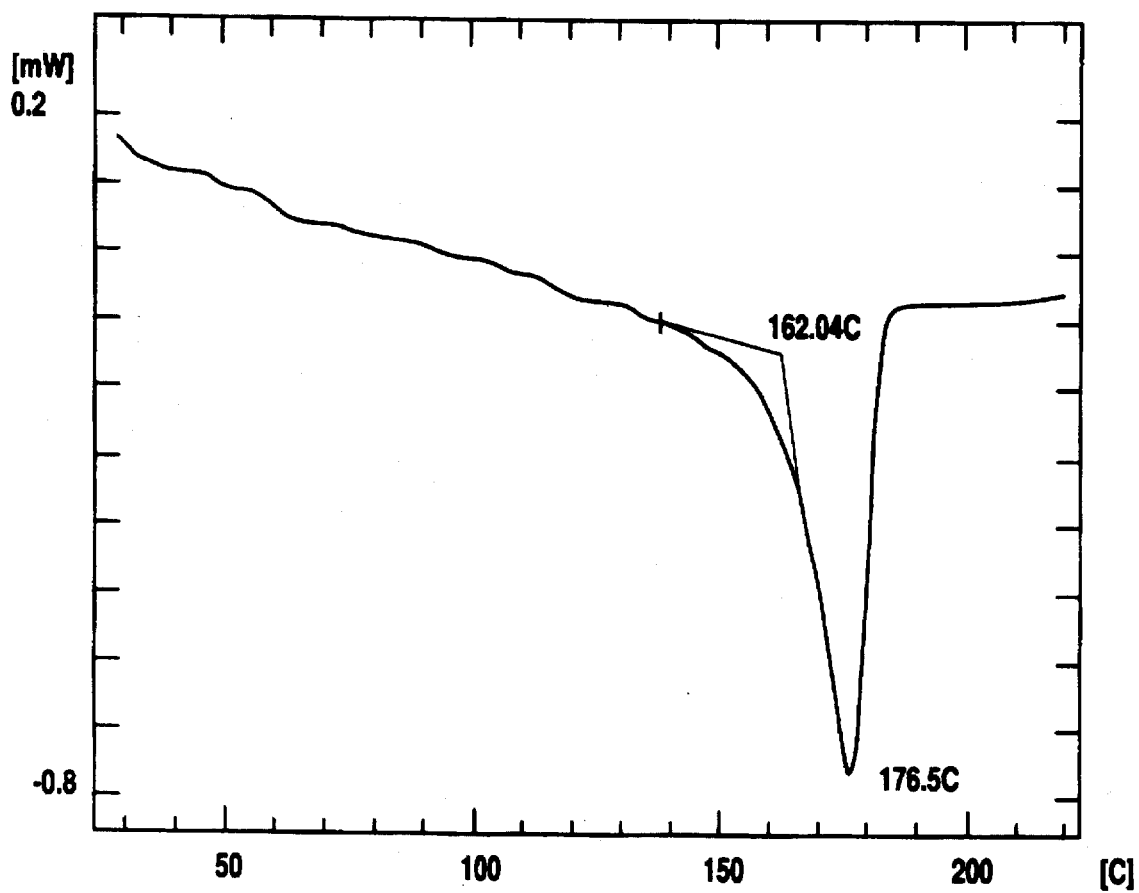
FIG. 5 is a characteristic differential scanning calorimetric thermogram of Form 2 showing the absence of peak 1 after heating.

DSC: Endotherms at 110.1° C. (onset at 102.4° C.) and at 175.1° C. (onset at 155.9° C.) (FIG. 3)

Figure 10:
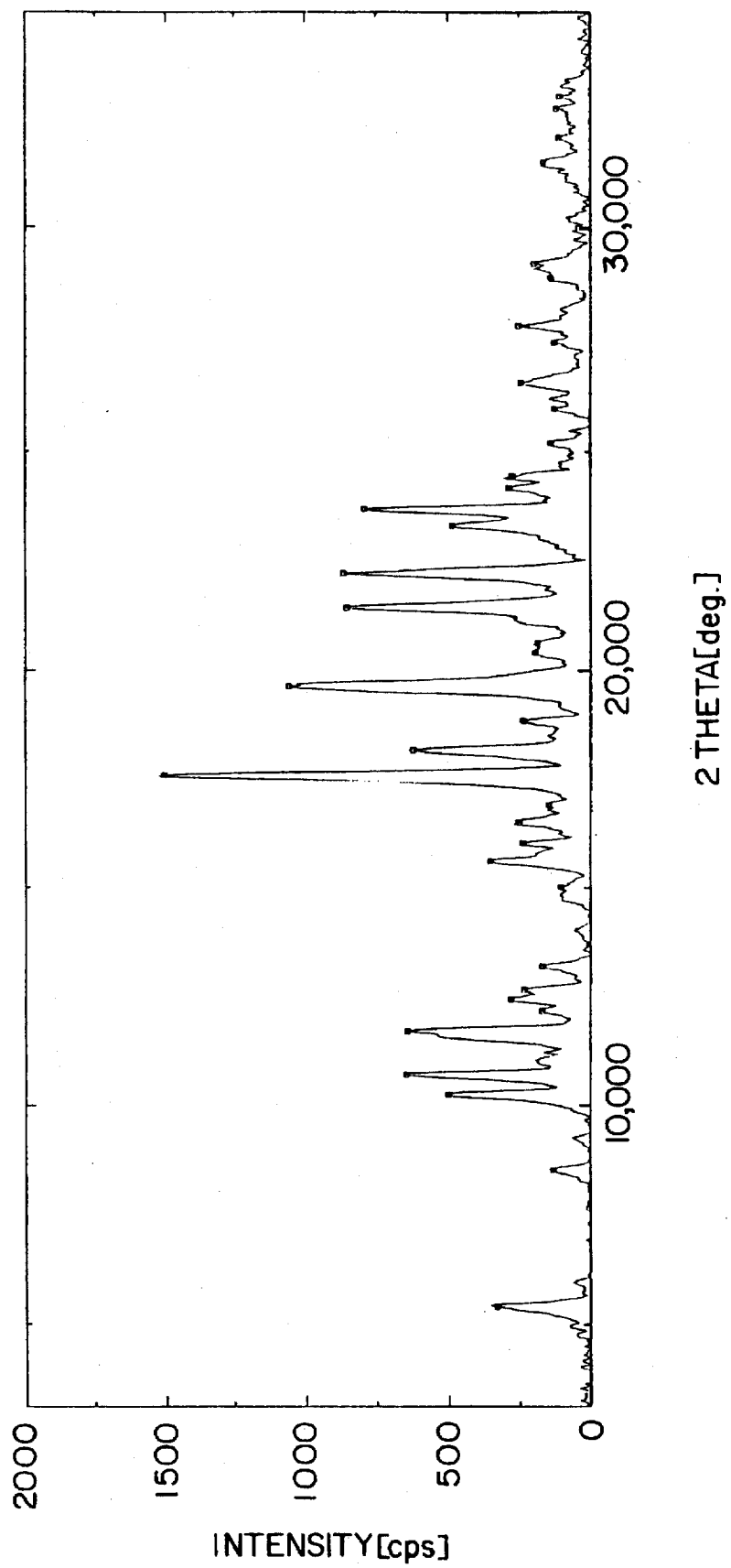
FIG. 10 is a characteristic X-ray powder diffraction pattern of Form 2.

X-ray powder diffraction (2θ): 5.40, 10.24, 10.70, 11.70, 12.18, 12.44, 12.66, 13.20, 15.60, 16.02, 16.50, 17.58, 18.16, 18.82, 19.62, 20.40, 20.64, 21.44, 22.22, 23.30, 23.68, 24.16, 24.44, 26.54, 27.82, 29.20, 31.48 (FIG. 10)

Figure 17:
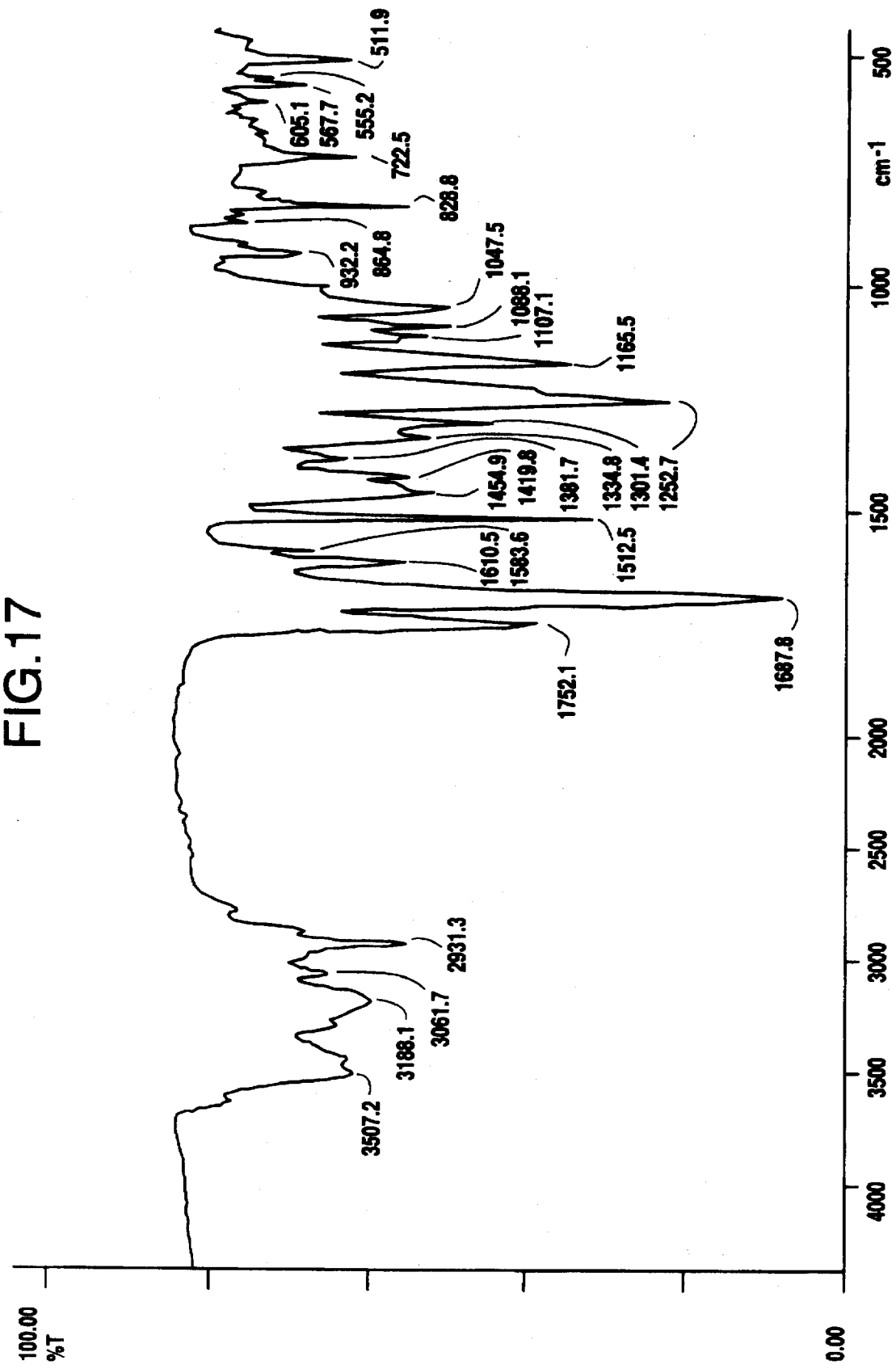
FIG. 17 is a characteristic infrared absorption spectrum of Form 2 in KBr.

Infrared absorption bands (cm$^{-1}$): 3506(w), 3187(w), 3061(w), 2931(w), 1751(m), 1688(s), 1610(w), 1583 (w), 1512(s), 1454(w), 1419(w), 1381(w), 1334(w), 1301(m), 1252(s), 1165(m), 1088(w), 1047(w), 932 (w), 828(w), 722(w), 511(w) (FIG. 17)

w=weak, m=medium, s=strong

According to yet another embodiment of the present invention, there is provided a process for the preparation of a novel polymorphic Form-3 of Troglitazone, having the formula I, which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent and (iv) scratching the resulting solution, while cooling rapidly to a temperature between 0° to −20° C. at a rate of 2° to 10° C./minute over a period in the range of 10–30 min. to precipitate the polymorphic Form-2 of Troglitazone.

(v) dissolving the polymorphic Form-2 of Troglitazone so obtained in step (iv) in an organic polar and/or medium polar solvent and heating the resulting solution with a non-polar solvent and (vi) heating the resulting solution on steam bath and cooling the solution slowly to room temperature at a rate of 0.1° to 1° C./minute over a period in the range of 24–72 h to crystallize the polymorphic Form-3 of Troglitazone which is characterized by the following data.

Figure 2:
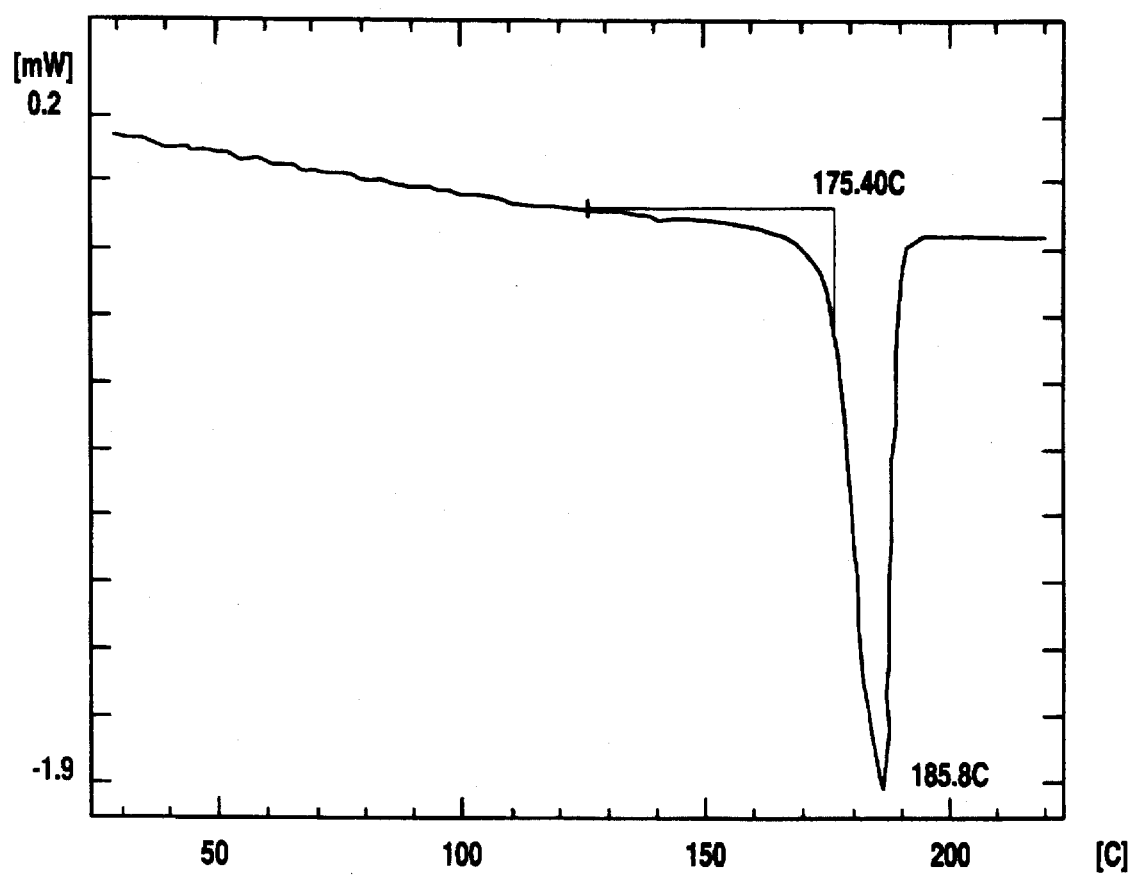
FIG. 2 is a characteristic differential scanning calorimetric thermogram of Form 3.

DSC: Endotherm at 185.8° C. (onset at 175:4° C.) (FIG. 2)

Figure 11:
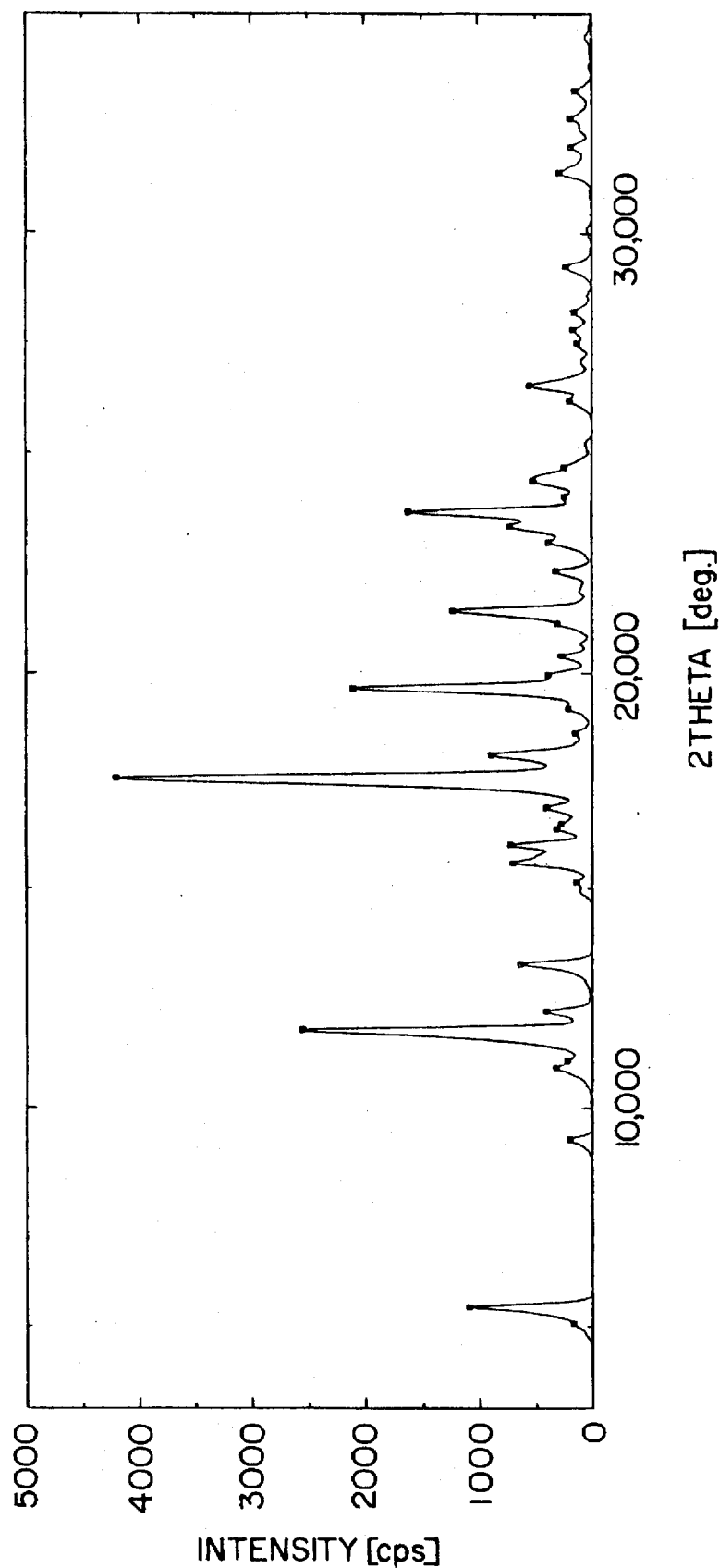
FIG. 11 is a characteristic X-ray powder diffraction pattern of Form 3.

X-ray powder diffraction (2θ): 5.45, 11.76, 13.24, 15.63, 16.03, 17.58, 18.13, 19.66, 21.42, 23.37, 23.67, 24.45, 26.53 (FIG. 11)

Figure 18:
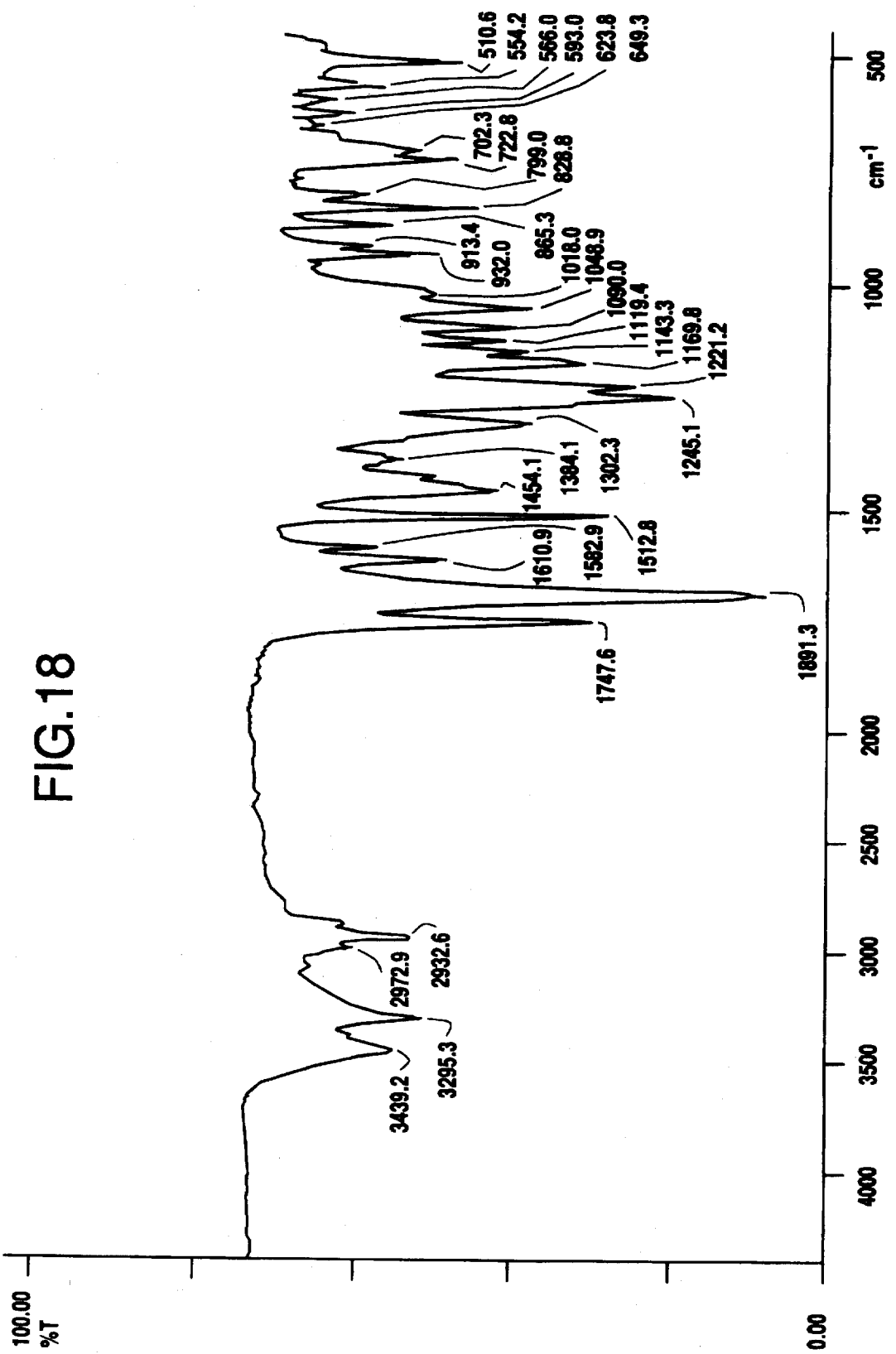
FIG. 18 is a characteristic infrared absorption spectrum of Form 3 in KBr.

Infrared absorption bands (cm$^{-1}$): 3439(w), 3295(w), 2972(w), 2932(w) 1747(m), 1690(s), 1611(w), 1582 (w), 1512(s), 1453(m), 1384(w), 1302(m), 1245(s), 1221(s), 1169(s), 1143(w), 1119(w), 1089(w), 1049 (w), 931(w), 828(w), 722(w), 510(w) (FIG. 18)

w=weak, m=medium, s=strong

According to yet another embodiment of the present invention, there is provided a process for the preparation of a novel polymorphic Form-4 of Troglitazone, having the formula I, which comprises (i) synthesizing Troglitazone, in erode form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent, (iv) cooling the resulting solution slowly to room temperature at a rate of 0.1° to 1° C./minute over a period in the range of 24–72 h to produce the polymorphic Form-1 of Troglitazone, (v) filtering the product and melting it by heating, (vi) cooling the melt to ambient temperature slowly at a rate of 0.1° to 1° C./minute over a period in the range of 1–4 h to give a glossy transparent material, grinding the transparent flake to a fine powder to yield the polymorphic Form-4 of Troglitazone which is characterized by the following data.

Figure 6:
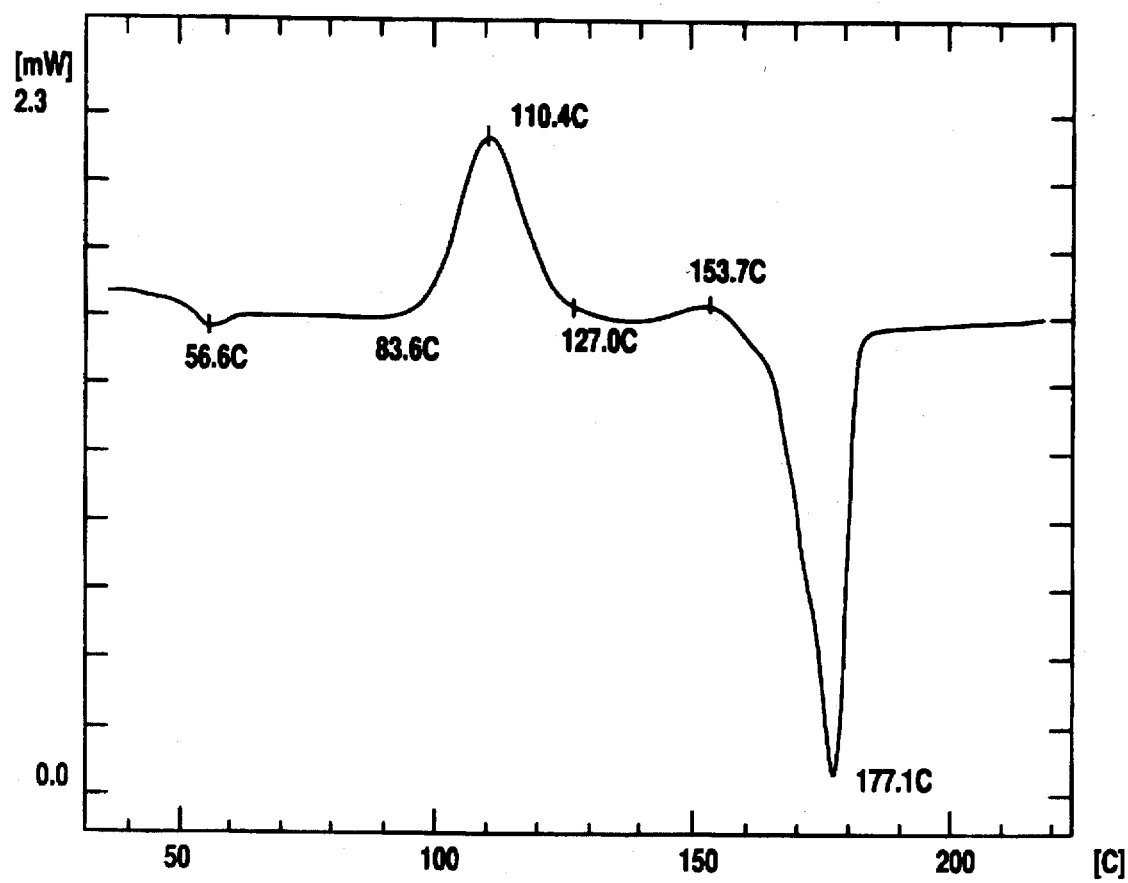
FIG. 6 is a characteristic differential scanning calorimetric thermogram of Form 4.

DSC: Endotherm at 56.6° C., exotherm at 110.4° C. (onset at 93.6° C.) and endotherm 177.1° C. (onset at 153.7° C.) (FIG. 6)

Figure 14:
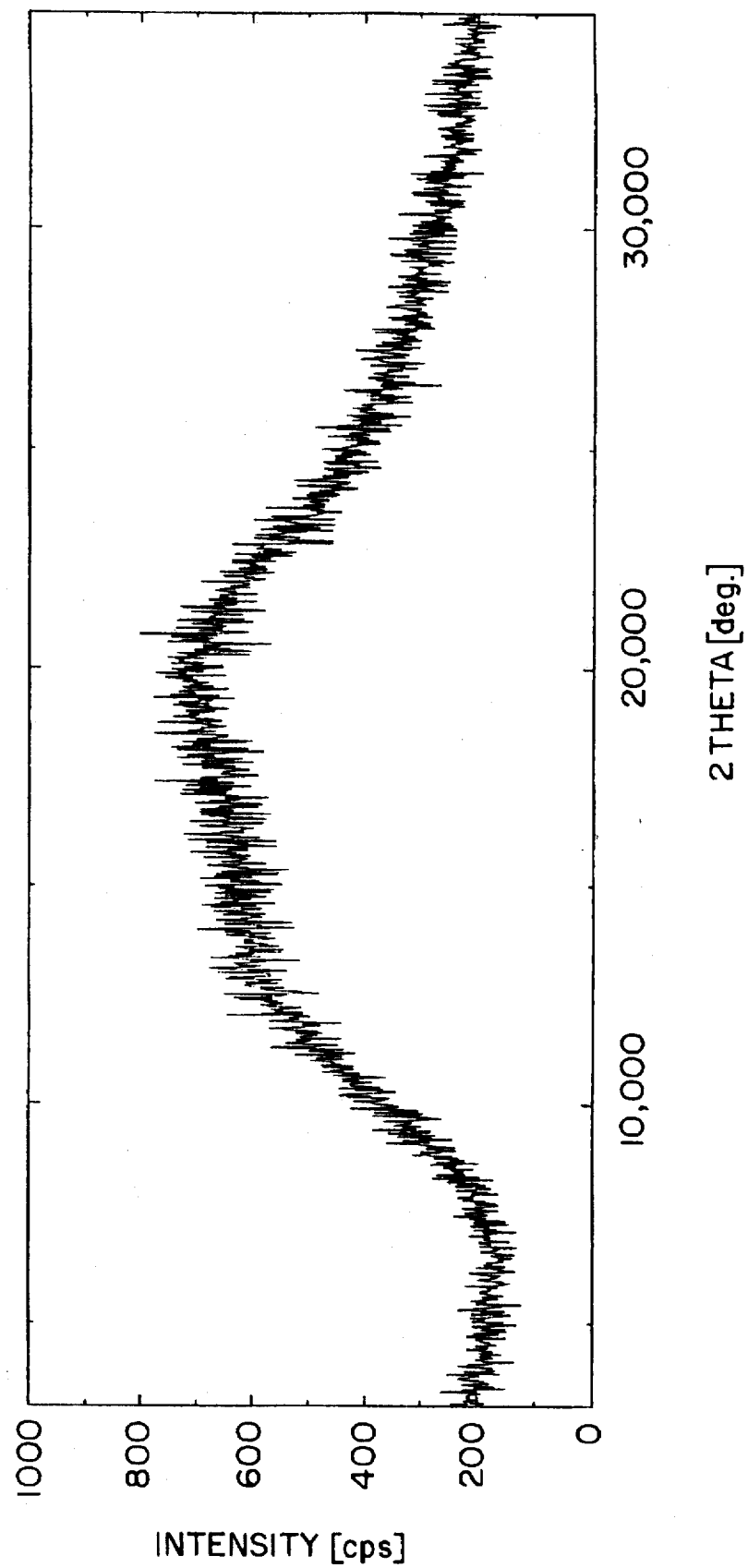
FIG. 14 is a characteristic X-ray powder diffraction pattern of Form 4.
Figure 15:
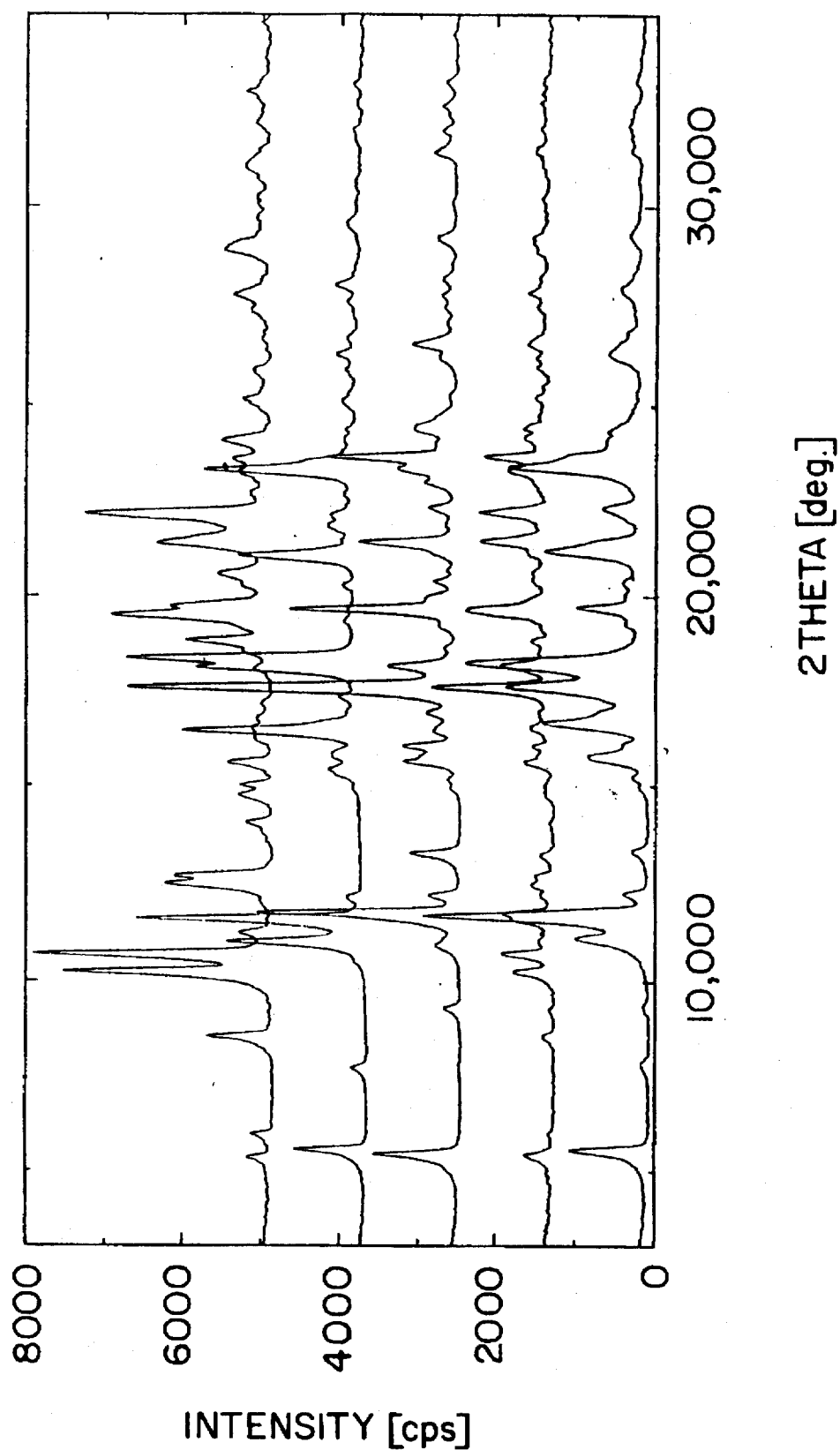
FIG. 15 is the multi-plot of X-ray powder diffraction patterns of Forms 1, 2, 3, 5, 6.

X-ray powder diffraction (2θ): No diffraction peaks due to its amorphous nature (FIG. 14)

Infrared absorption bands (cm$^{-1}$): 3473(w), 3204(w), 3060(w), 2924(w) 1754(m), 1696(s), 1610(w), 1583

Figure 19:
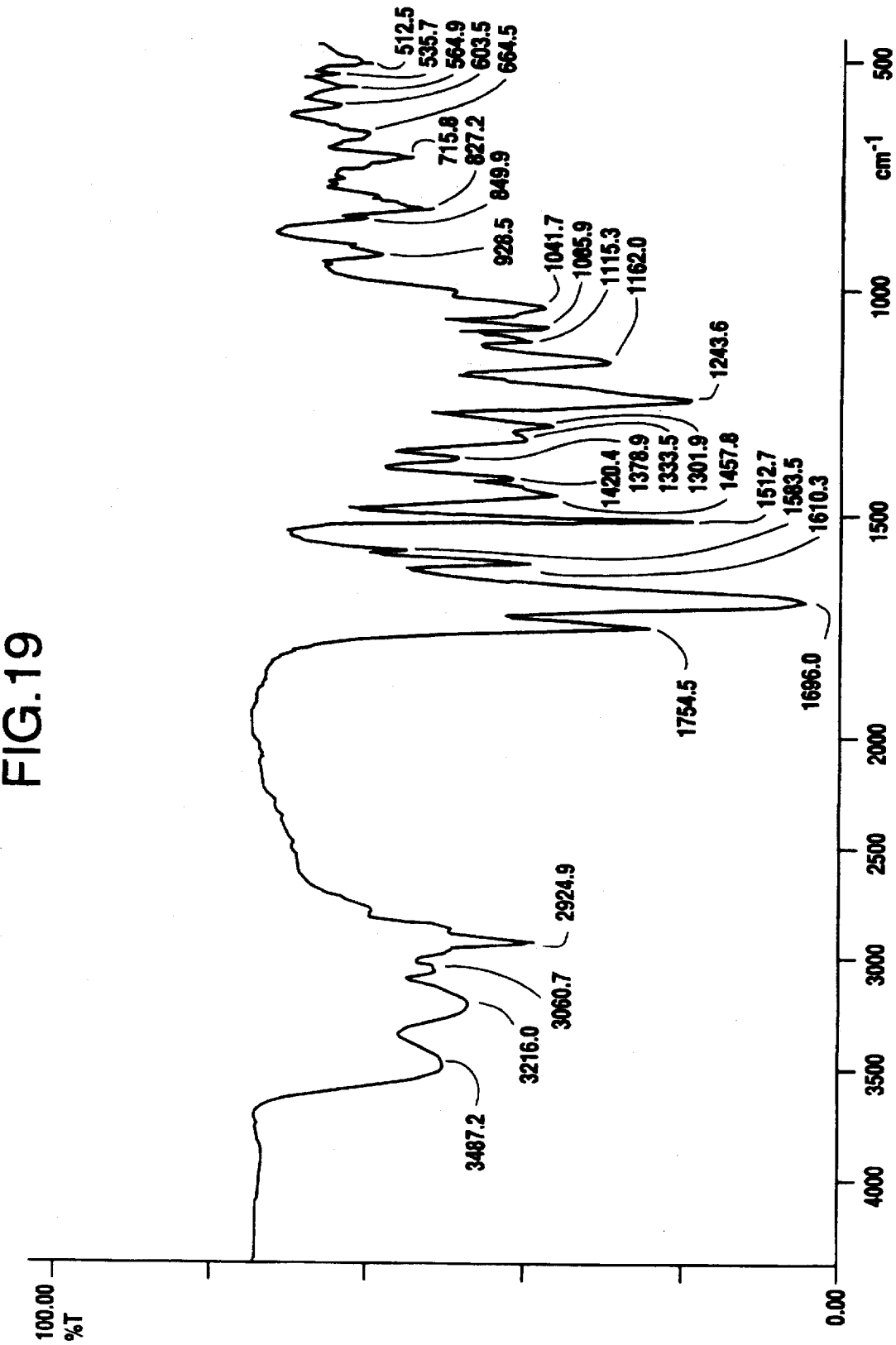
FIG. 19 is a characteristic infrared absorption spectrum of Form 4 in KBr.

(w), 1512(s), 1457(m), 1420(w), 1378(w), 1333(m), 1301(m), 1243(s), 1162(m), 1115(w), 1085(w), 1041 (w), 928(w), 849(w), 827(w), 715(w), 664(w), 512 (w) (FIG. 19)

w=weak, m=medium, s=strong

According to yet another embodiment of the present invention, there is provided a process for the preparation of the novel polymorphic Form-4 of Troglitazone, having the formula I, which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent, (iv) scratching while cooling rapidly to a temperature in the range of 0° to −20° C. at a rate of 2° to 10° C./minute, over a period in the range of 10–30 min. to precipitate the polymorphic Form-2 of Troglitazone, (v) filtering the product and melting it by heating, (vi) cooling the melt to ambient temperature slowly at a rate of 0.1° to 1° C./minute over a period in the range of 1–4 h to give a glossy transparent material, (vii) grinding the transparent flake to a fate powder to yield the polymorphic Form-4 of Troglitazone which is characterized by the data presented in the previous method.

According to yet another embodiment of the present invention, there is provided a process for the preparation of the novel polymorphic Form-4 of Troglitazone, having the formula I, which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent, (iv) scratching the resulting solution, while cooling rapidly to a temperature in the range of 0° to −20° C. at a rate of 2° to 10° C./minute, over a period in the range of 10–30 min. to precipitate the polymorphic Form-2 of Troglitazone, (v) dissolving the polymorphic Form-2 of Troglitazone so obtained in step (iv), in an organic polar and/or medium polar solvent and heating the resulting solution with a non-polar solvent, (vi) heating the resulting solution preferably on steam bath and cooling the solution slowly to room temperature at a rate of 0.1° to 1° C./minute, over a period in the range of 24–72 h to crystallize the polymorphic Form-3 of Troglitazone, (vii) filtering the product and melting it by heating, (viii) cooling the melt to ambient temperature slowly at a rate of 0.1° to 1° C./minute, over a period in the range of 1–4 h to give a glossy transparent material, (ix) grinding the transparent flake to a fine powder to yield the polymorphic Form-4 of Troglitazone which is characterized by the data presented in the previous method.

According to a further embodiment of the present invention, there is provided a process for the preparation of a novel polymorphic Form-5 of Troglitazone having the formula I,, which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent, (iv) cooling the resulting solution slowly to room temperature at a rate of 0.1° to 1° C./minute over a period in the range of 24–72 h to produce the polymorphic Form-1 of Troglitazone, (v) filtering the product and melting it by heating, (vi) cooling the melt to ambient temperature at a rate of 0.1° to 1° C./minute over a period in the range of 1–4 h to give a glossy transparent material, (vii) grinding the transparent flake to a fine powder to yield the polymorphic Form-4 of Troglitazone, (viii) subjecting the polymorphic Form-4 of Troglitazone so obtained in step (vii) to isothermal heating in the range of 60° to 170° C. preferably at 130° C., for a period in the range of 5 min. to 4 h, cooling to ambient temperature slowly at a rate of 0.1° to 1° C./minute, over a period in the range of 1–4 h, followed by grinding the flake to a fine powder to yield the polymorphic Form-5 of Troglitazone which is characterized by the following data.

Figure 7:
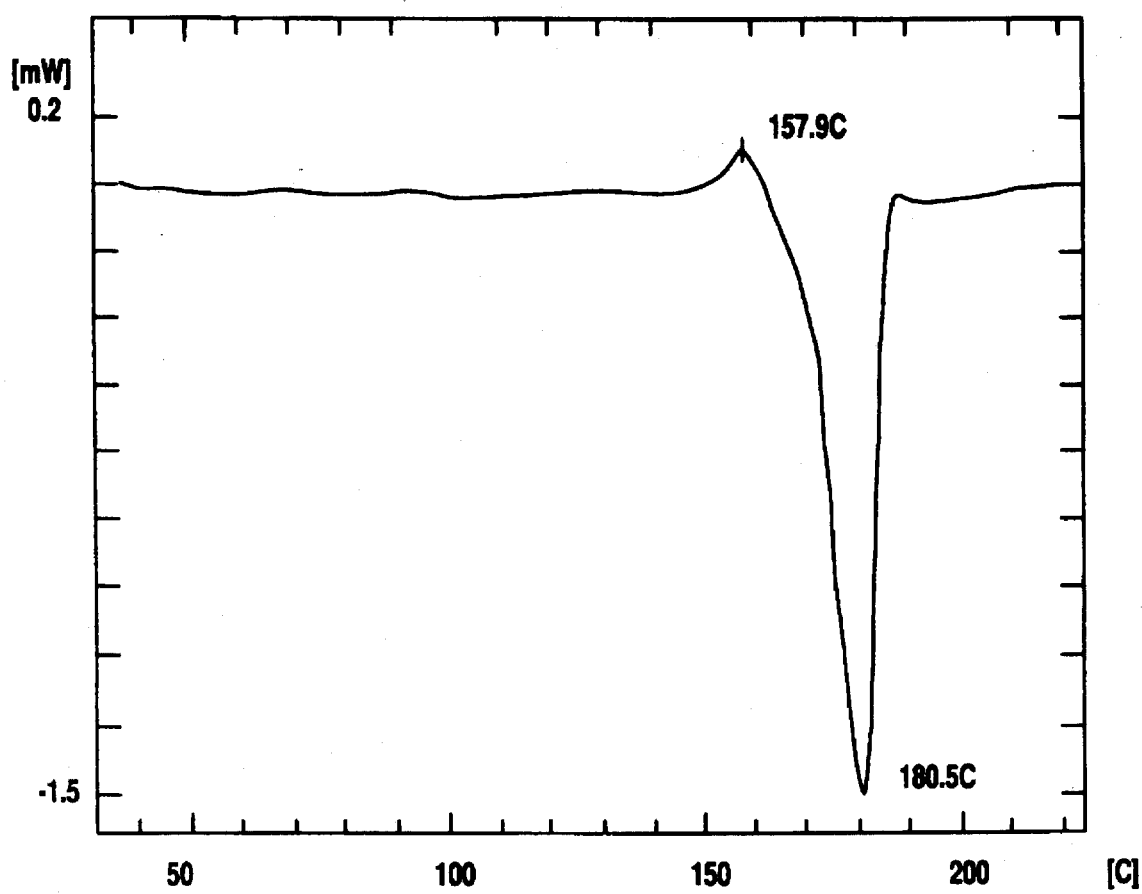
FIG. 7 is a characteristic differential scanning calorimetric thermogram of Form 5.

DSC: Endotherm at 180.5° C. (onset at 157.9° C.) (FIG. 7)

Figure 12:
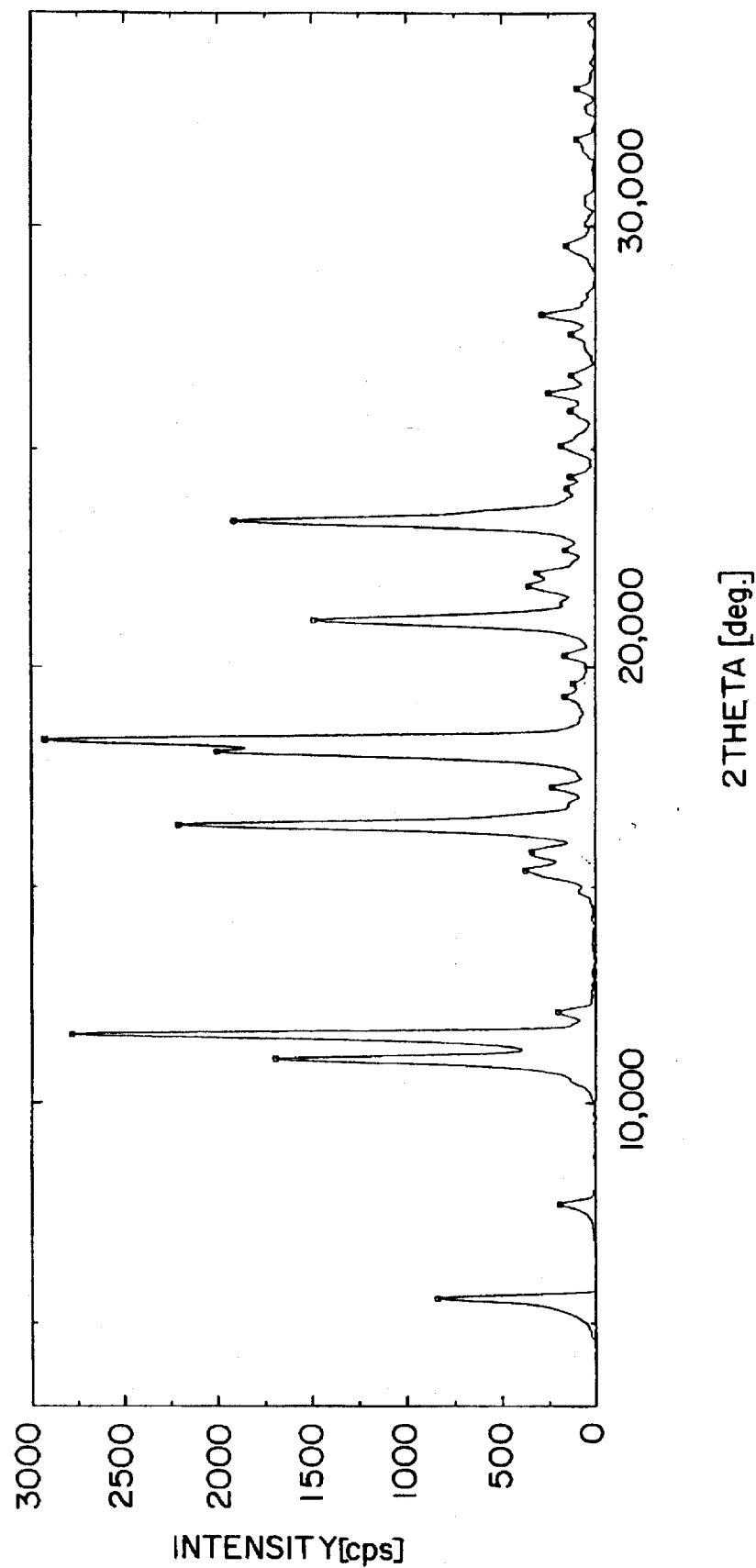
FIG. 12 is a characteristic X-ray powder diffraction pattern of Form 5.

X-ray powder diffraction (2θ): 5.56, 11.02, 11.58, 15.38, 15.80, 16.42, 18.08, 18.34, 21.06, 21.84, 22.14, 23.32 (FIG. 12)

Figure 20:
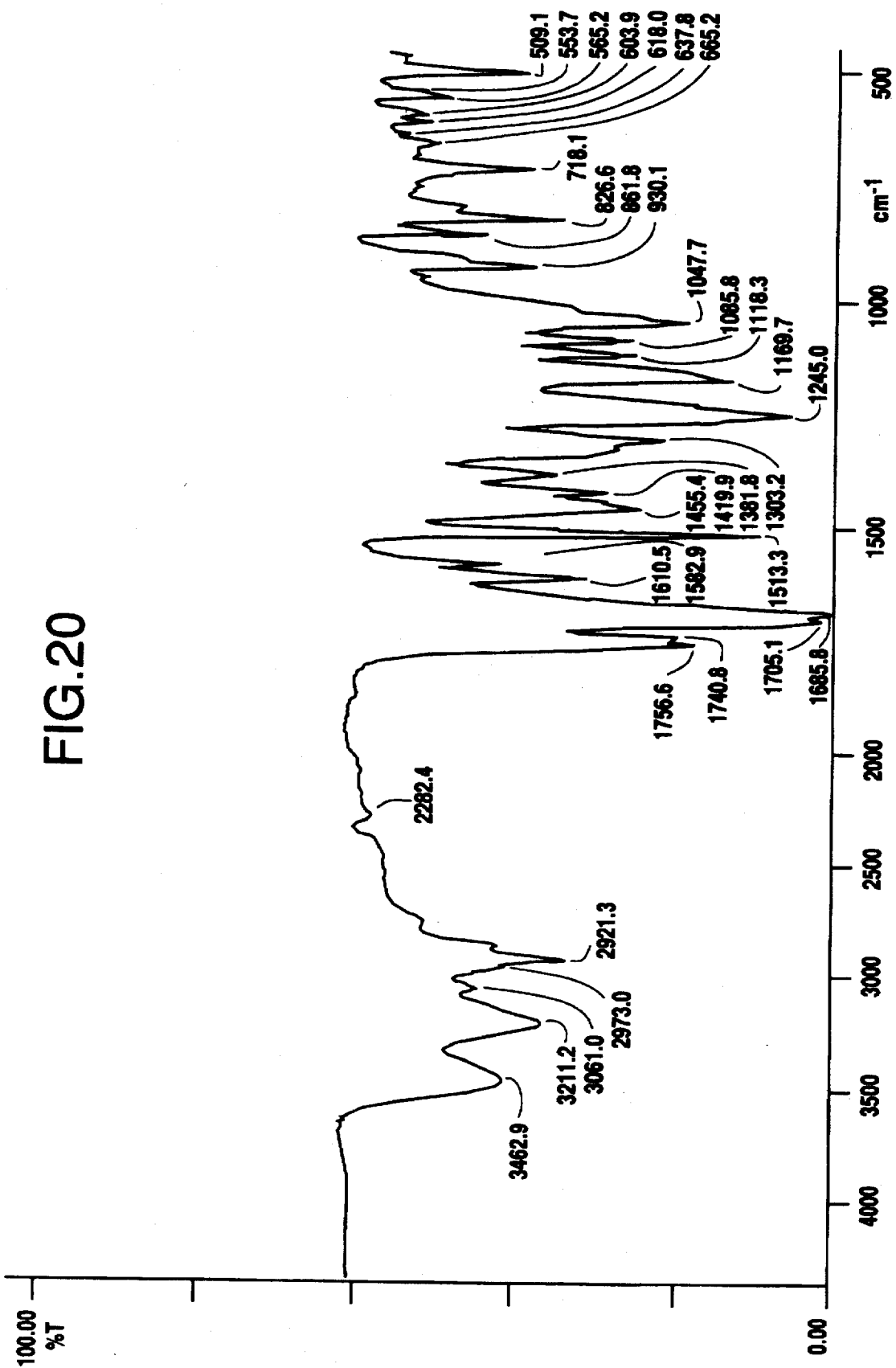
FIG. 20 is a characteristic infrared absorption spectrum of Form 5 in KBr.

Infrared absorption bands ($cm^{-1}$): 3462(w), 3211(w), 3060(w), 2921(w) 1756(m), 1685(s), 1610(w), 1583 (w), 1513(s), 1454(m), 1419(w), 1381(w), 1303(m), 1244(s), 1168(m), 1117(w), 1085(w), 1047(m), 929 (w), 861(w), 825(w), 718(w), 665(w), 564(w), 509 (w) (FIG. 20)

w=weak, m=medium, s=strong

According to a further embodiment of the present invention, there is provided a process for the preparation of a novel polymorphic Form-5 of Troglitazone having the formula I,, which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent, (iv) scratching while cooling rapidly to a temperature in the range of 0° to −20° C. at a rate of 2° to 10° C./minute, over a period in the range of 10–30 min. to precipitate the polymorphic Form-2 of Troglitazone, (v) filtering the product and melting it by heating, (vi) cooling the melt to ambient temperature slowly at a rate of 0.1° to 1° C./minute, over a period in the range of 1–4 h to give a glossy transparent material, (vii) grinding the transparent flake to a fine powder to yield the polymorphic Form-4 of Troglitazone, (vii) subjecting the polymorphic Form-4 of Troglitazone so obtained in step (vii) to isothermal heating in the range of 60° to 170° C. preferably at 130° C. for a period in the range of 5 min to 4 h, cooling to ambient temperature at a rate of 0.1 to 1° C./minute, over a period in the range of 1–4 h followed by grinding the flake to a free powder to yield the polymorphic Form-5 of Troglitazone which is characterized by the data presented in the previous method.

According to a further embodiment of the present invention, there is provided a process for the preparation of a novel polymorphic Form-5 of Troglitazone having the formula I, which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and heating the resulting solution with a non-polar solvent, (iv) scratching the resulting solution, while cooling rapidly to a temperature in the range of 0° to −20° C. at a rate of 2°–10° C./minute, over a period in the range of 10–30 min; to precipitate the polymorphic Form-2 of Troglitazone, (v) dissolving the polymorphic Form-2 of Troglitazone so obtained in step (iv) in an organic polar and/or medium polar solvent and heating the resulting solution with a non-polar solvent, (vi) heating the resulting solution preferably on a steam bath and cooling the solution slowly to room temperature at a rate of 0.1° to 1° C./minute, over a period in the range of 24–72 h to crystallize the polymorphic Form-3 of Troglitazone, (vii) filtering the product and melting it by heating, (viii) cooling the melt to ambient temperature at a rate of 0.1° to 1° C./minute, over a period in the range of 1–4 h to give a glossy transparent material, grinding the transparent flake to a fine powder to yield the polymorphic Form-4 of Troglitazone, (ix) subjecting the polymorphic Form-4 of Troglitazone obtained in step (ix) to isothermal heating in the range of 60° to 170° C. preferably at 130° C. for a period in the range of 5 min. to 4 h, cooling to ambient temperature slowly at a rate of 0.1° to 1° C./minute, over a period in the range of 1–4 h followed by grinding the flake to a fine powder to yield the polymorphic Form-5 of Troglitazone which is characterized by the data presented in the previous method.

According to yet another embodiment of the present invention there is provided a process for the preparation of novel polymorphic Form-6 of Troglitazone having the formula I which comprises (i) synthesizing Troglitazone, in crude form employing known methods, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar and/or medium polar solvent and adding a non-polar solvent to the resulting solution and (iv) cooling the resulting solution rapidly to −5° C. at a rate of 10° C./minute and maintaining the temperature at −5° C. for a period of 10–16 h to produce the polymorphic Form-6 of Troglitazone which is characterized by the following data.

Figure 8:
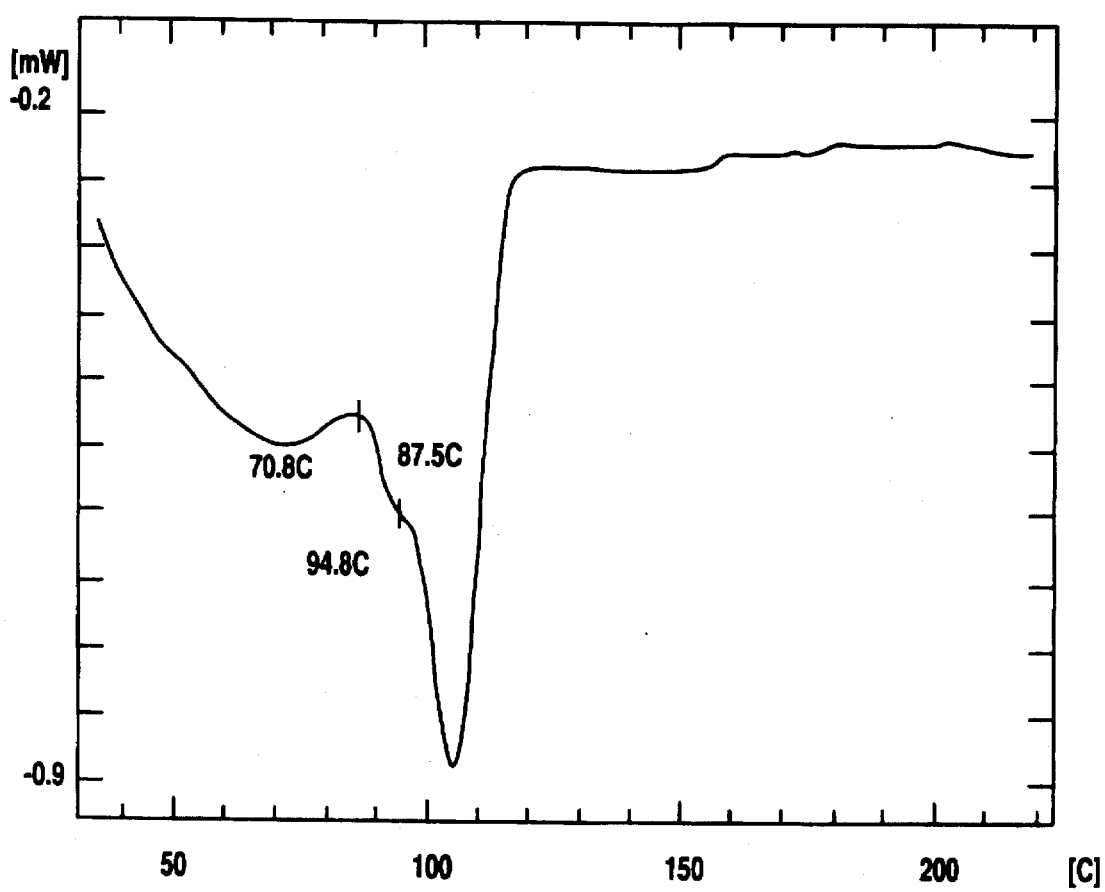
FIG. 8 is a characteristic differential scanning calorimetric thermogram of Form 6.

DSC: Endotherm at 105.4° C. (onset at 94.8° C.) (FIG. 8)

Figure 13:
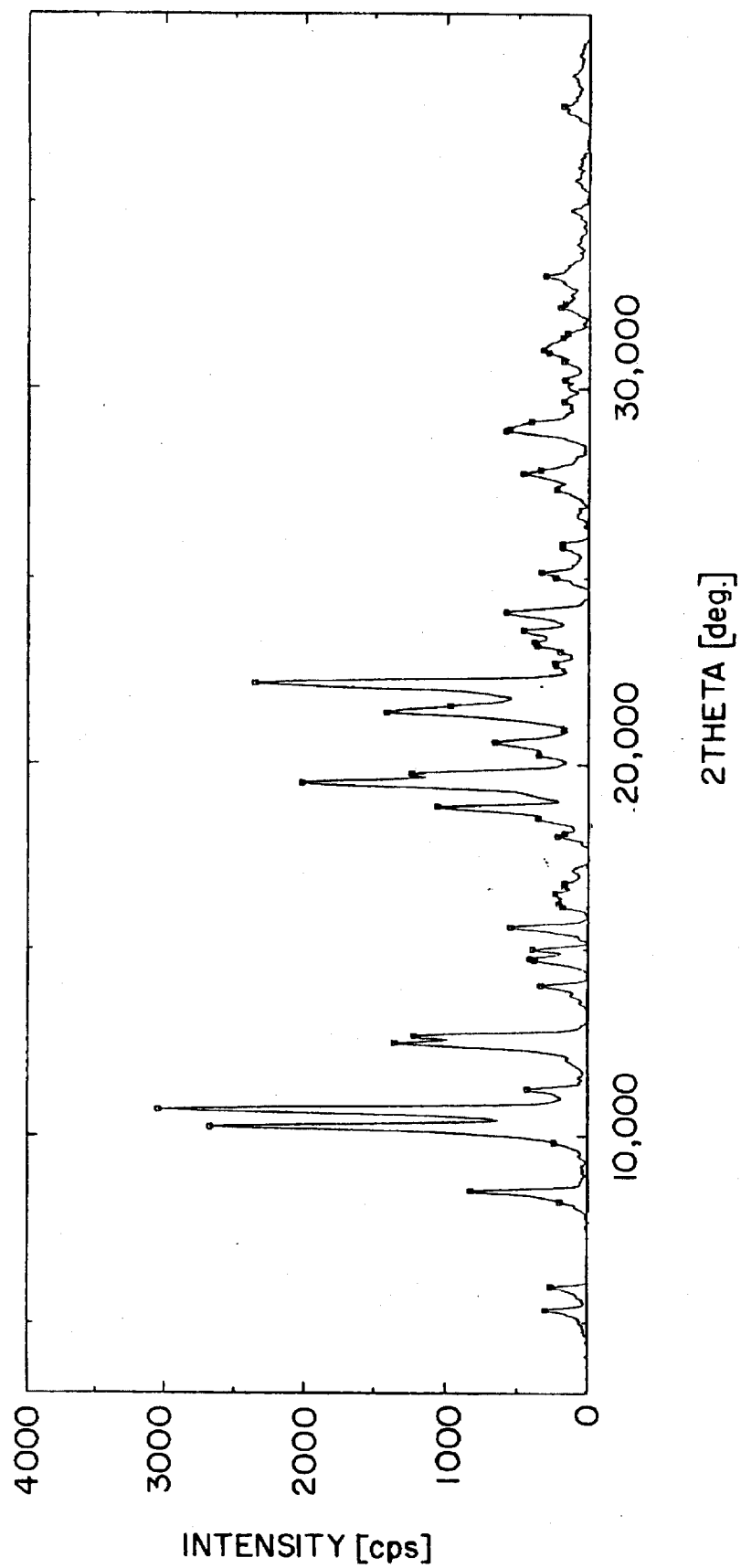
FIG. 13 is a characteristic X-ray powder diffraction pattern of Form 6.

X-ray powder diffraction (2θ): 8.54, 10.24, 10.70, 11.24, 12.48, 12.68, 14.04, 14.70, 14.74, 15.00, 15.58, 18.52, 18.84, 19.48, 19.74, 20.24, 20.58, 21.38, 21.56, 22.18, 23.20, 23.30, 23.62, 24.10, 25.16, 27.76, 27.86, 28.88, 28.92, 29.12, 31.02 (FIG. 13 )

Figure 21:
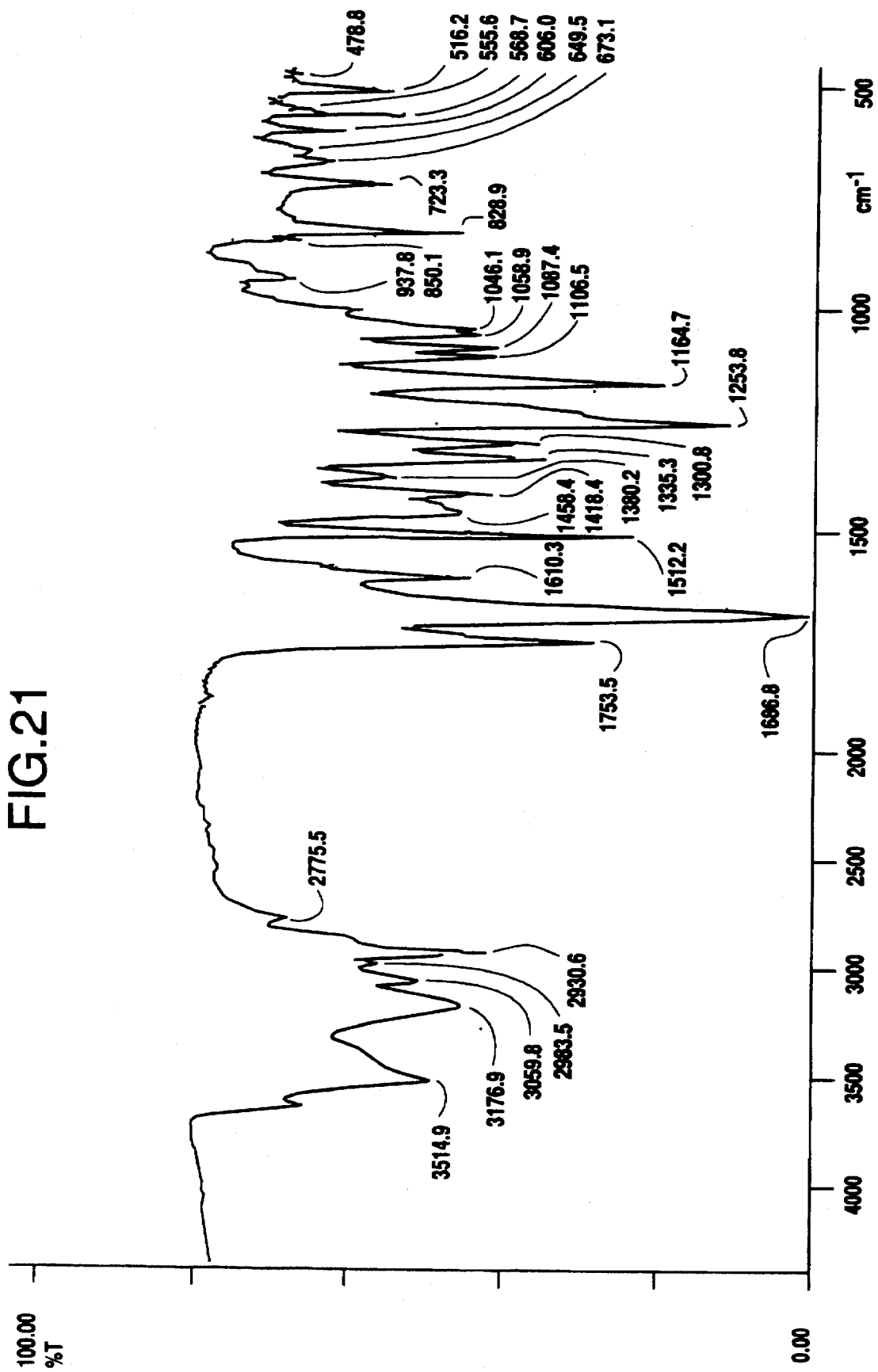
FIG. 21 is a characteristic infrared absorption spectrum of Form 6 in KBr.
Figure 22:
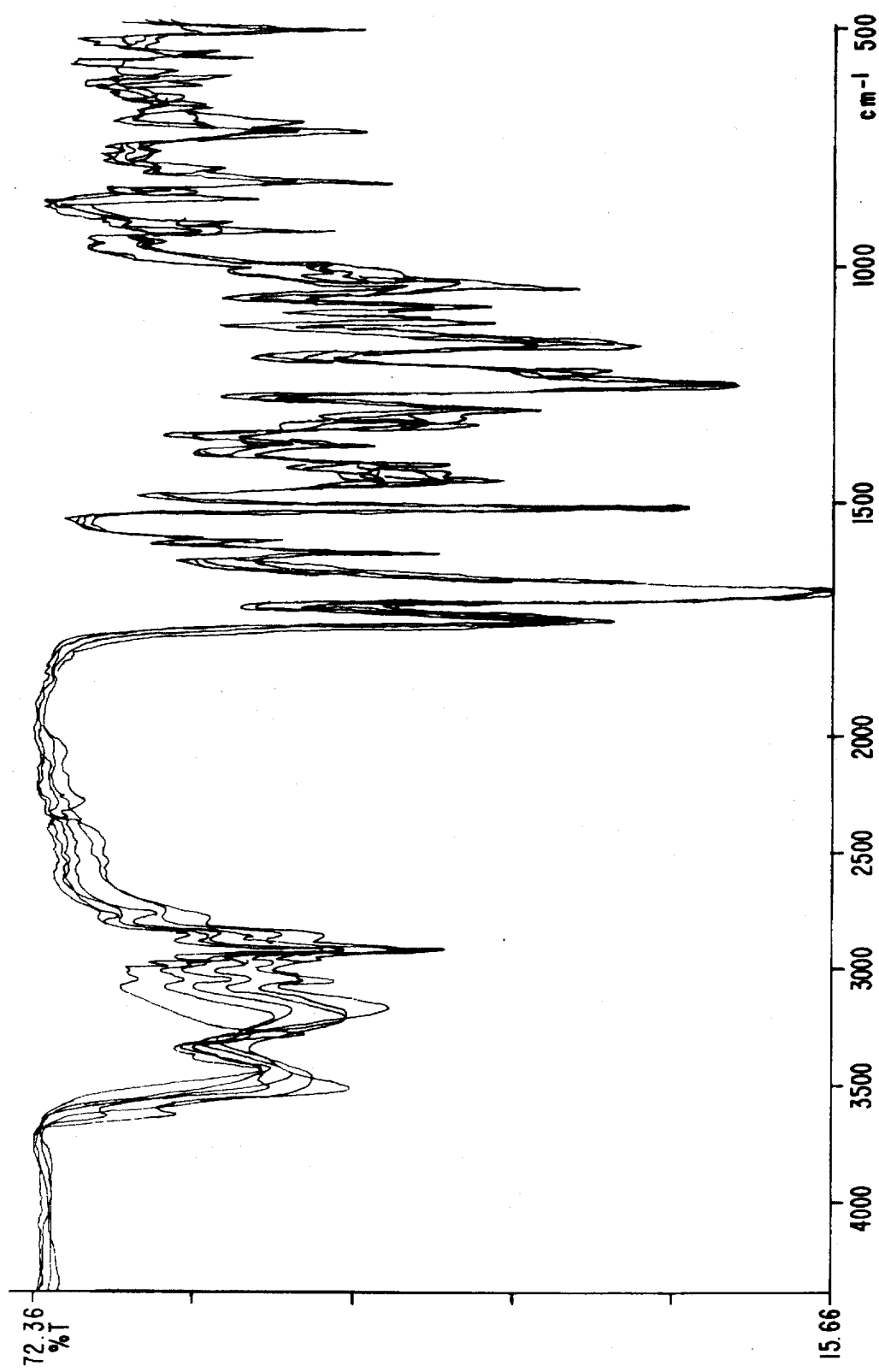
FIG. 22 is the multi-plot of infrared absorption spectra of Forms 1, 2, 3, 4, 5, 6 (4000–500 $cm^{-1}$). Common colour code for FIGS. 22–26: Black—Form 1; Orange—Form 2; Red—Form 3; Violet—Form 4; Blue—Form 5; Green—Form 6.
Figure 23:
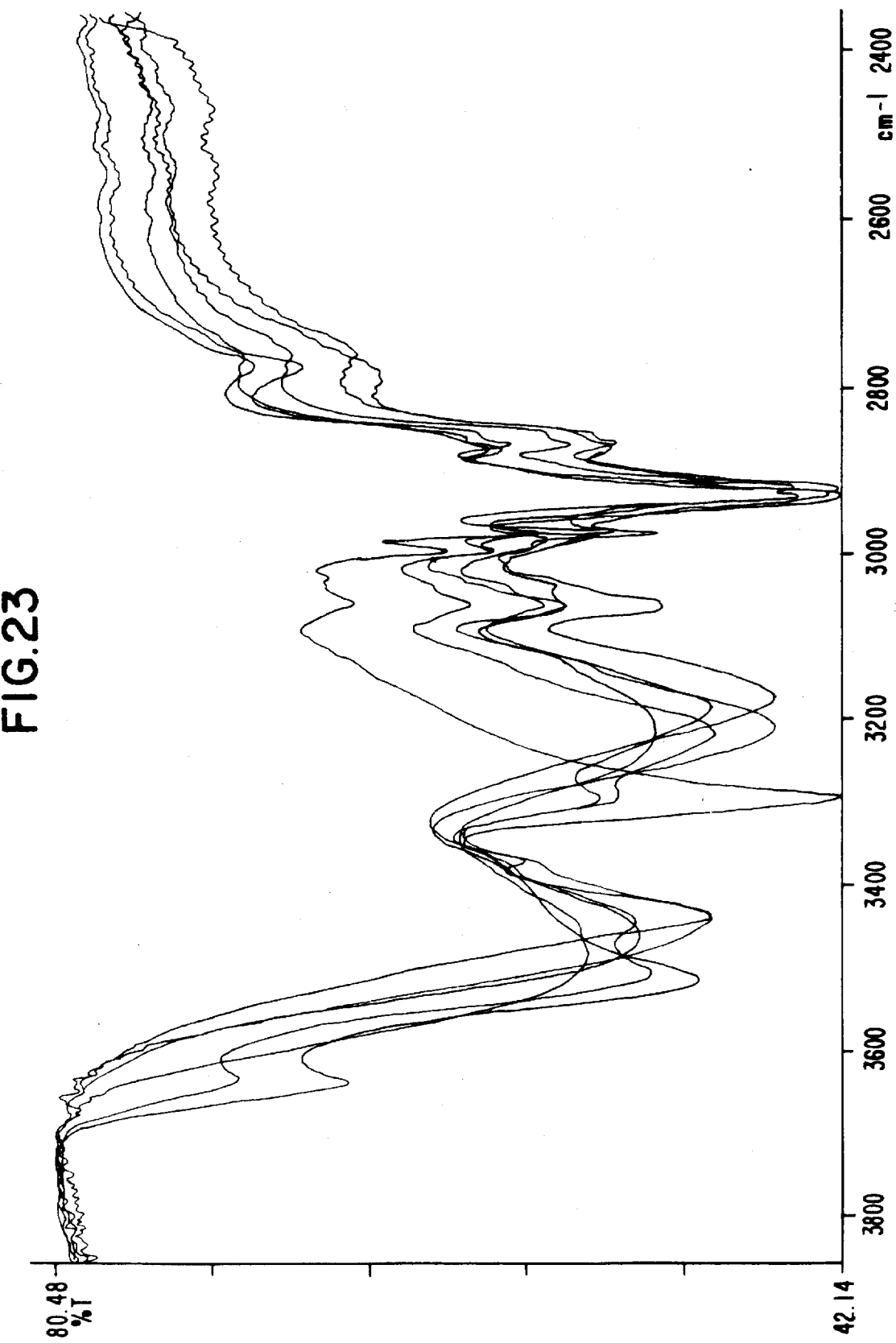
FIG. 23 is the multi-plot of infrared absorption spectra of Forms 1, 2, 3, 4, 5, 6 (3800–2400 $cm^{-1}$).
Figure 24:
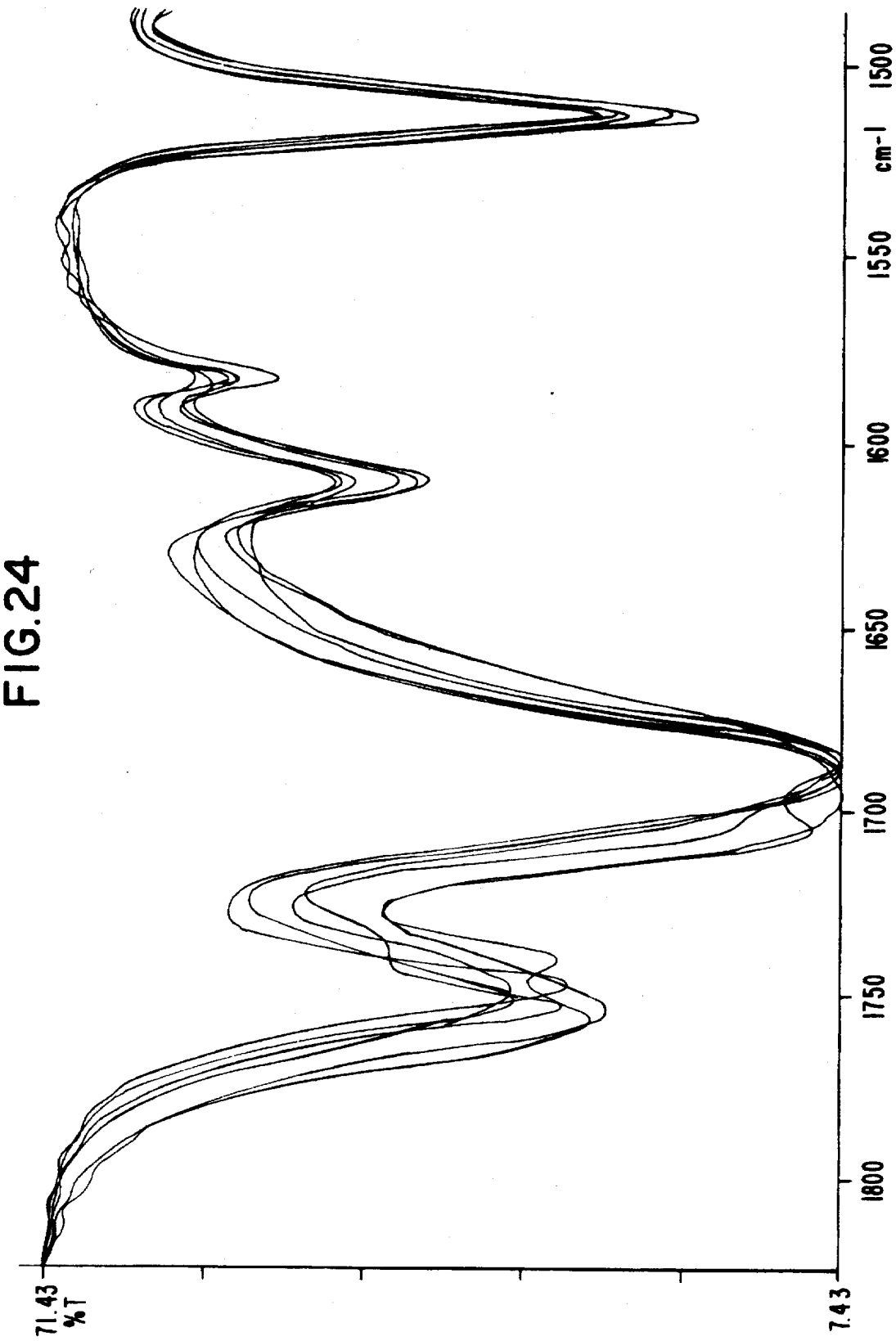
FIG. 24 is the multi-plot of infrared absorption spectra of Forms 1, 2, 3, 4, 5, 6 (1800–1500 $cm^{-1}$).
Figure 25:
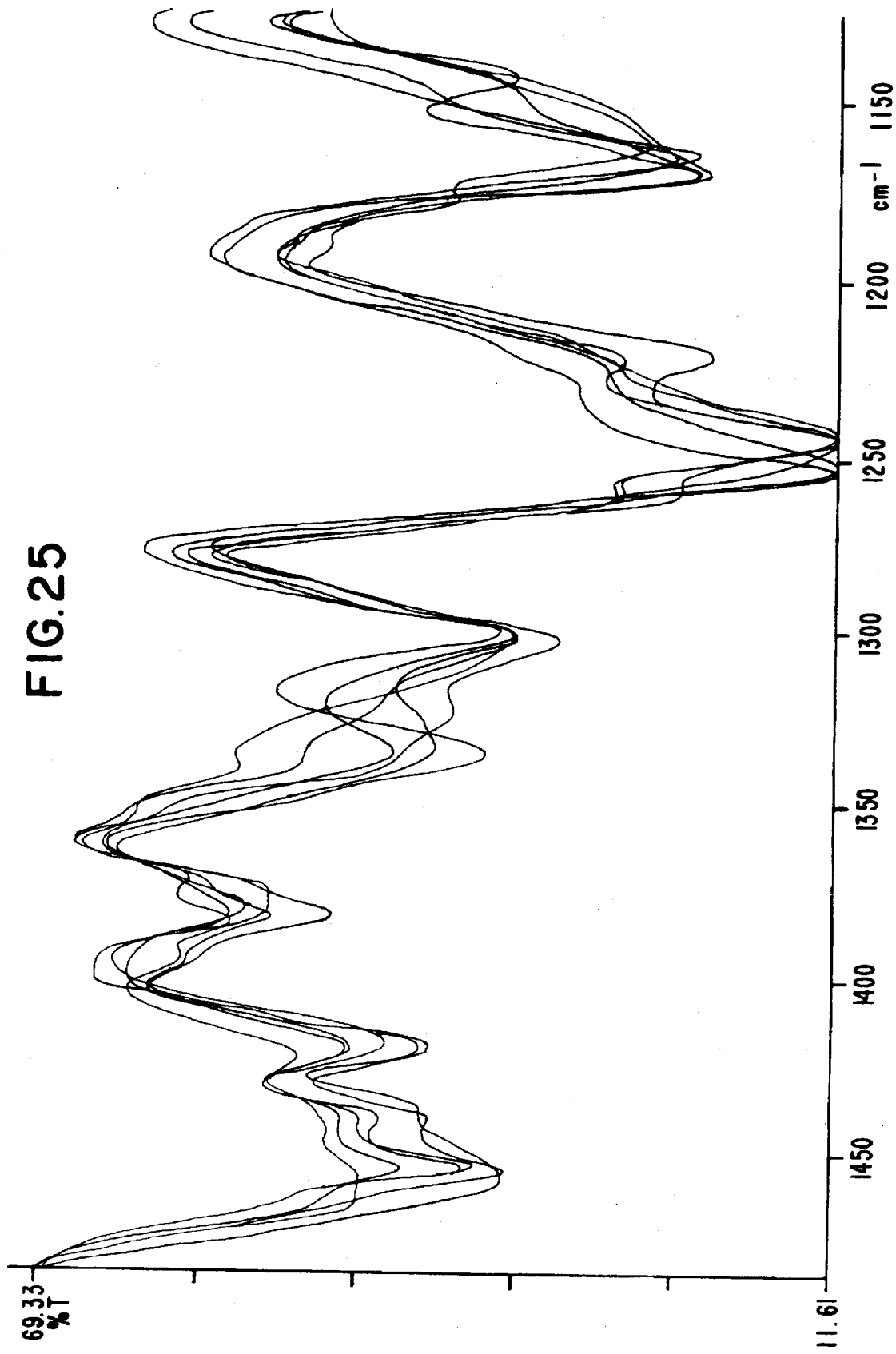
FIG. 25 is the multi-plot of infrared absorption spectra of Forms 1, 2, 3, 4, 5, 6 (1500–1100 $cm^{-1}$).
Figure 26:
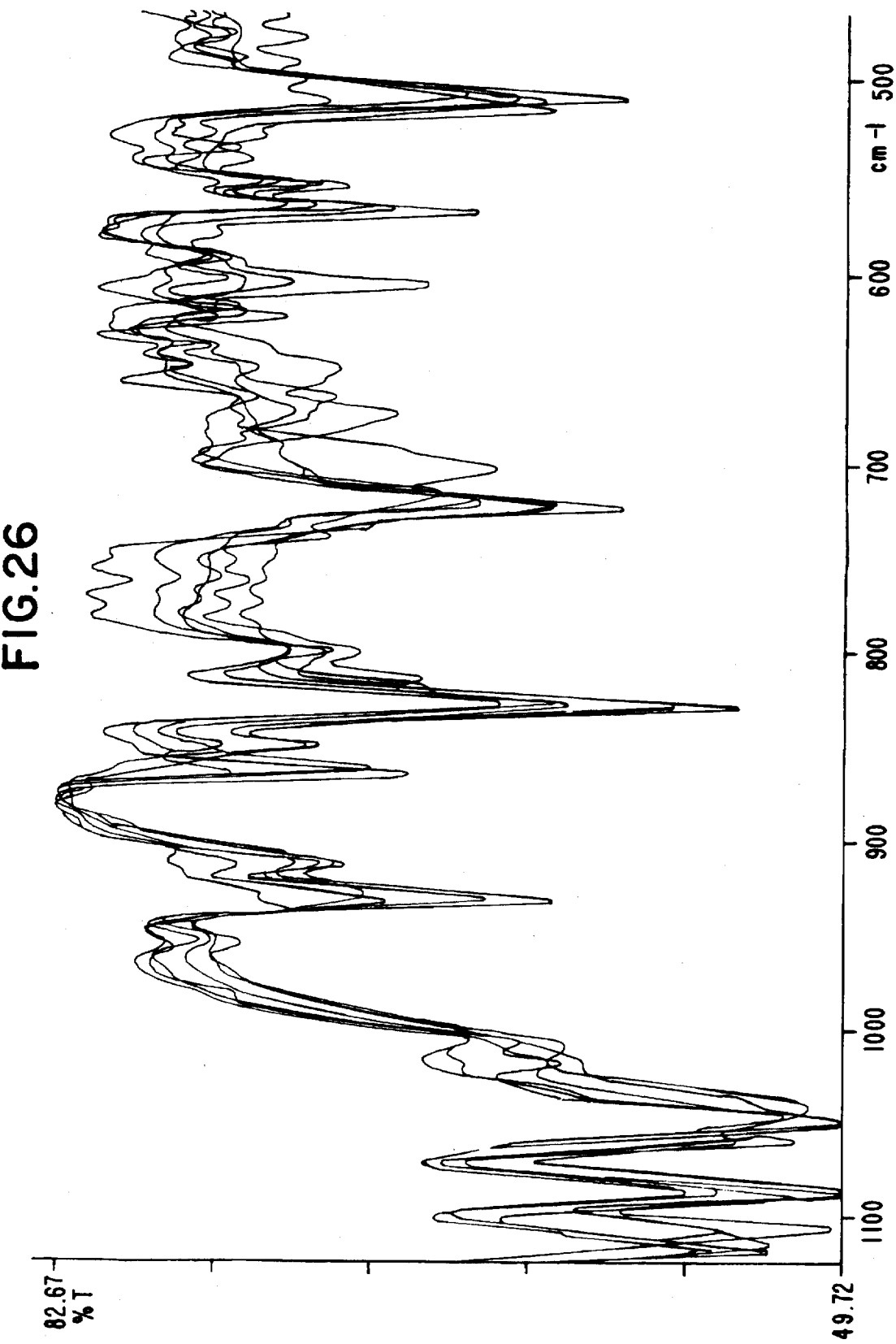
FIG. 26 is the multi-plot of infrared absorption spectra of Forms 1, 2, 3, 4, 5, 6 (1125–500 $cm^{-1}$).

Infrared absorption bands (cm$^{-1}$): 3634(w), 3514(w), 3176(w), 3060(w), 2930(w), 1753(m), 1686(s), 1610 (w), 1512(s), 1459(w), 1418(w), 1380(w), 1335(m), 1300(m), 1253(s), 1164(s), 1106(w), 1087(w), 1058 (w), 1048(w), 937(w), 828(m), 723(w), 673(w), 606 (w), 568(w), 515(w). (FIG. 21)

w=weak, m=medium, s=strong

According to yet another embodiment of the present invention, there is provided a process for the preparation of the novel polymorphic Form-4 of Troglitazone, having the formula I, which comprises (i) melting the polymorphic Form-5 of Troglitazone prepared by any one of the processes described above, by heating.

(ii) cooling the melt to ambient temperature slowly at a rate of 0.1° to 1° C./minute, over a period in the range of 1–4 h to give a glossy transparent material, (iii) grinding the transparent flake to a fine powder to yield the polymorphic Form-4 of Troglitazone which is characterized by the data presented earlier.

According to yet another embodiment of the present invention, there is provided a process for the preparation of the novel polymorphic Form-4 of Troglitazone, having the formula I, which comprises (i) melting the polymorphic Form-6 of Troglitazone prepared by the process described above, by heating.

(ii) cooling the melt to ambient temperature slowly at a rate of 0.1° to 1° C./minute, over a period in the range of 1–4 h to give a glossy transparent material, (iii) grinding the transparent flake to a fine powder to yield the polymorphic Form-4 of Troglitazone which is characterized by the data presented earlier.

According to yet another embodiment of the present invention, there is provided a process for the preparation of the novel polymorphic Form-5 of Troglitazone, having the formula I, which comprises (i) melting the polymorphic Form-6 of Troglitazone prepared by the process described above, by heating.

(ii) cooling the melt to ambient temperature slowly at a rate of 0.1° to 1° C./minute, over a period in the range of 1–4 h to give a glossy transparent material, (iii) grinding the transparent flake to a fine powder to yield the polymorphic Form-4 of Troglitazone.

(iv) subjecting the polymorphic Form-4 of Troglitazone obtained in step (iii) to isothermal heating in the range of 60° to 170° C. preferably at 130° C. for a period in the range of 5 min. to 4 h, cooling to ambient temperature slowly at a rate of 0.1° to 1° C./minute, over a period in the range of 1–4 h followed by grinding the flake to a fine powder to yield the polymorphic Form-5 of Troglitazone which is characterized by the data presented in the previous method.

The organic polar and/or medium polar solvents are selected from acetonitrile, ethanol, methanol, acetone, 1,4-dioxane, methyl ethyl ketone, ethylacetate, chloroform, tetrahydrofuran, n-propanol, isopropanol, 1,2-dichloroethane, dichloromethane, diethylether, benzene, etc. while the non-polar solvents are selected from hexane, heptane, cyclohexane, carbontetrachloride, toluene, xylene, etc.

The present invention is described in detail with examples given below that are provided by way of illustration only and therefore should not be construed to limit the scope of the invention.

Process for the preparation of crude Troglitazone of ~70% HPLC purity, the starting material for the preparation of novel polymorphic forms according to the present invention

EXAMPLE-1

A mixture of 70 g of ethyl-3-[4-(6-acetoxy-2,5,7,8-tetramethylchroman-2-ylmethoxy)phenyl]-2-chloropropionate, 13.12 g of thiourea and 80.2 ml of sulpholane was reacted for 80 min., under a nitrogen stream at 115°–120° C. Subsequently, a 656.2 ml Acetic acid, 218.7 ml conc. hydrochloric acid and 109.4 ml water was added to this and the resulting mixture was further heated for 12 hrs at 85°–90° C. The reaction mixture was cooled to room temperature and 196.8 g of sodium bicarbonate was added and once the evolution of carbondioxide had ceased, the solvent was distilled off applying high vacuum. A 10:1 by volume mixture of benzene and ethyl acetate was added to the residue and the crude product was washed with a mixture of equal volumes of a saturated aq. sodium bicarbonate solution & water. The organic layer was dried over anhydrous sodium sulphate and the solvent was distilled off. The resulting crude product was quickly eluted from a silica gel column with 50% ethylacetate-hexane to furnish 40 g of the required 5-{4-(6-hydroxy-2, 5, 7, 8-tetramethylchroman-2-yl-methoxy) benzyl} thiazolidine-2,4-dione (Troglitazone) with a HPLC purity of ~67–70%. The elution of column was continued further to yield 5-[4-(6-hydroxy-2,5,7,8-tetramethylchroman-2-yl-methoxy)benzyl]2-iminothiazolidine-4-one with HPLC purity of ~70%.

Examples 2–4 illustrate the process for the preparation of the polymorphic Form-1 of Troglitazone

EXAMPLE-2

55 g of the crude Troglitazone obtained by the process as described in Example-1 was adsorbed on 60–120 mesh silicagel and extracted first with hexane using a soxhlet and then with benzene. Hexane extract mostly contained the less polar impurities while the benzene extract contained the required product. The benzene extract was concentrated and dried so as to remove traces of benzene. The gummy material was taken up in dichloromethane and stirred vigorously to obtain a clear solution. The solution was allowed to stand at room temperature for a period of 48 hrs to yield 40 g of >99% pure polymorphic Form-1 of Troglitazone.

EXAMPLE-3

15.5 g of 5-[4-(6-hydroxy-2,5,7,8-tetramethyl chroman-2-yl-methoxy) benzyl]-2-iminothiazolidine-4-one, prepared by the process as described in Example-1, was added to a mixture of 225 ml of acetic acid, 75 ml of conc. hydrochloric acid and 40 ml of water and the mixture was refluxed for 12 hrs. The reaction mixture was cooled to room temperature and 66.2 g of sodium bicarbonate was added and once the evolution of carbondioxide had ceased, the solvent was distilled off applying high vacuum. A 10:1 by volume mixture of benzene and ethyl acetate was added to the residue and the crude product was washed with a mixture of equal volumes of a saturated aq. sodium bicarbonate solution & water. The organic layer was dried over anhydrous sodium sulphate and the solvent was distilled off. The resulting crude product was quickly eluted tom a silica gel column with 50% ethylacetate-hexane to furnish 12.5 g of the required 5-{4-(6-hydroxy-2, 5, 7, 8-tetramethylchroman-2-yl-methoxy) benzyl) thiazolidine-2,4-dione (Troglitazone) with a HPLC purity of ~67–70%.

5 g of crude Troglitazone so obtained was taken in ~1 ml of acetone and ~100 ml benzene was added and heated on a steam bath till the solid dissolved completely. The clear solution was filtered and allowed to cool to room temperature at a rate of 0.1 to 1° C./minute over a period of 48 h to yield 2.5 g of >99% pure polymorphic Form-1 of Troglitazone.

EXAMPLE-4

5 g of crude Troglitazone obtained by the process as described in Example-1 was taken in ~100 ml benzene and heated on steam bath till the solid completely dissolved and the clear solution was allowed to cool to room temperature at a rate of 0.1° to 1° C./minute during a period ~36 h to give 2.5 g of >99% pure polymorphic Form-1 of Troglitazone.

Examples 5–8 illustrate the process for the preparation of the polymorphic Form-2 of Troglitazone

EXAMPLE-5

55 g of the crude Troglitazone obtained by the process as described in Example-1 was adsorbed on 60–120 mesh silicagel and extracted first with hexane using a soxhlet and then with benzene. Hexane extract mostly contained the less polar impurities while the benzene extract contained the required product. The benzene extract was concentrated and dried so as to remove traces of benzene. The gummy material was taken up in dichloromethane and stirred vigorously to obtain a clear solution. The solution was rapidly cooled to −10° C., at a rate of 10° C./minute, over a period of 15 min. while scratching to yield 40 g of >99% pure polymorphic Form-2 of Troglitazone.

EXAMPLE-6

15.5 g of 5-[4-(6-hydroxy-2,5,7,8-tetramethyl chroman-2-yl-methoxy) benzyl]-2-iminothiazolidine-4-one, prepared by the process as described in Example-1, was added to a mixture of 225 ml of acetic acid, 75 ml of conc. hydrochloric acid and 40 ml of water and the mixture was refluxed for 12 hrs. The reaction mixture was cooled to room temperature and 66.2 g of sodium bicarbonate was added and once the evolution of carbondioxide had ceased, the solvent was distilled off applying high vacuum. A 10:1 by volume mixture of benzene and ethyl acetate was added to the residue and the crude product was washed with a mixture of equal volumes of a saturated aq. sodium bicarbonate solution & water. The organic layer was dried over anhydrous sodium sulphate and the solvent was distilled off. The resulting crude product was quickly eluted from a silica gel column with 50% ethylacetate-hexane to furnish 12.5 g of the required 5-{4-(6-hydroxy-2, 5, 7, 8-tetramethylchroman-2-yl-methoxy) benzyl) thiazolidine-2,4-dione (Troglitazone) with a HPLC purity of ~67–70%.

5 g of crude Troglitazone so obtained was taken in ~1 ml of acetone and ~100 ml benzene was added and heated on a steam bath till the solid dissolved completely. The solution was rapidly cooled to −10° C., at a rate of 10° C./minute, over a period of 15 min. while scratching to yield 2.5 g of >99% pure polymorphic Form-2 of Troglitazone.

EXAMPLE-7

5 g of crude Troglitazone obtained by the process as described in Example-1 was taken in ~100 ml benzene and heated on steam bath till the solid completely dissolved. The solution was rapidly cooled to −10° C., at a rate of 10° C./minute, over a period of 15 min. while scratching to yield 40 g of >99% pure polymorphic Form-2 of Troglitazone.

EXAMPLE-8

5 g of crude Troglitazone obtained by the process as described in Example-1 and 5 ml acetone were taken in 100 ml round bottom flask and stirred on a magnetic stirrer till all the solid dissolved in acetone. Acetone was completely removed under vacuum at 50° C. and then ~25 ml dichloromethane was added to the gummy residue and stirred at 5° C. for ½–1 hr. ~50 ml of Pet ether was added and scratched the walls of the container. Stirring at 5° C. was continued for another 1 hr. The solid was filtered and dried to yield 2.7 g >99% pure polymorphic Form-2 of Troglitazone.

Example 9 illustrates the process for the preparation of the polymorphic Form-3 of Troglitazone

EXAMPLE-9

10 g of the polymorphic Form-2 of Troglitazone obtained by the process as described in Example-8, was dissolved in 25 ml acetone and the solvent was completely removed. ~50 ml benzene was added to the gummy mass and heated on a stem bath for 15–30 min. The clear solution was cooled to 5° C. at a rate of 1° C./minute during a period of 24 h to yield 5 g of >99% pure polymorphic Form-3 of Troglitazone.

Examples 10–14 illustrate the process for the preparation of the polymorphic Form-4 of Troglitazone

EXAMPLE-10

5 g the polymorphic Form-1 of Troglitazone obtained by the process described in Example-2, was heated to melt and the resulting transparent flake was crushed to give an yellowish white flue powder of the polymorphic Form-4 of Troglitazone in near quantitative yield. This material exhibited typical liquid crystalline/amorphous nature.

EXAMPLE-11

5 g of the polymorphic Form-2 of Troglitazone obtained by the process described in Example-5, was heated to melt and the resulting transparent flake was crushed to yield an yellowish white powder of the polymorphic Form-4 of Troglitazone in near quantitative yield which was found to be similar in all respects to the product obtained in Example-10.

EXAMPLE-12

5 g of the polymorphic Form-3 of Troglitazone obtained by the process described in Example-9, was heated to melt and the resulting transparent flake was crushed to yield an yellowish white powder of the polymorphic Form-4 of Troglitazone in near quantitative yield which was found to be similar in all respects to the product obtained in Example-10 and 11.

EXAMPLE-13

5 g of the polymorphic Form-5 of Troglitazone was heated to melt and the resulting transparent flake was crushed to yield an yellowish white powder of the polymorphic Form-4 of Troglitazone in near quantitative yield which was found to be similar in all respects to the product obtained in Examples 10–12.

EXAMPLE-14

5 g of the polymorphic Form-6 of Troglitazone was heated to melt and the resulting transparent flake was crushed to yield an yellowish white powder of the polymorphic Form-4 of Troglitazone in near quantitative yield which was found to be similar in all respects to the product obtained in Examples 10–13.

Examples 15–19 illustrate the process for the preparation of the polymorphic Form-5 of Troglitazone

EXAMPLE 15

5 g of the polymorphic Form-1 of Troglitazone obtained by the process described in Example-1, was heated to melt and the resulting transparent flake was crushed to give an yellowish white fine powder of the polymorphic Form-4 of Troglitazone in near quantitative yield. The polymorphic Form-4 of Troglitazone thus obtained was heated isothermally at a temperature in the range of 60° to 170° C. preferably 130° C. for a period in the range of 5 min. to 4 h, cooled to room temperature at a rate of 0.1° to 1° C./minute and crushed the resulting material to give the polymorphic Form-5 of Troglitazone in near quantitative yield.

EXAMPLE-16

5 g of the polymorphic Form-2 of Troglitazone, obtained by the process described in Example-5, was heated to melt and the resulting transparent flake was crushed to give an yellowish white fine powder of the polymorphic Form-4 of Troglitazone in near quantitative yield. The polymorphic Form-4 of Troglitazone thus obtained was heated isothermally at a temperature in the range of 60° to 170° C. preferably 130° C. for a period in the range of 5 min. to 4 h, cooled to room temperature at a rate of 0.1° to 1° C./minute and crushed the resulting material to give the polymorphic Form-5 of Troglitazone in near quantitative yield.

EXAMPLE-17

5 g of the polymorphic Form-3 of Troglitazone obtained by the process described in Example-9, was heated to melt and the resulting transparent flake was crushed to give an yellowish white fine powder of the polymorphic Form-4 of Troglitazone in near quantitative yield. The polymorphic Form-4 of Troglitazone thus obtained was heated isothermally at a temperature in the range of 60° to 170° C. preferably 130° C. for a period in the range of 5 min. to 4 h, cooled to room temperature at a rate of 0.1° to 1° C./minute and crushed the resulting material to give the polymorphic Form-5 of Troglitazone in near quantitative yield.

EXAMPLE-18

5 g of the polymorphic Form-4 of Troglitazone obtained by the process described in Example-11, was heated isothermally at a temperature in the range of 60° to 170° C. preferably 130° C. for a period in the range of 5 min. to 4 h, cooled to room temperature at a rate of 0.1° to 1° C./minute and crashed the resulting material to give the polymorphic Form-5 of Troglitazone in near quantitative yield.

EXAMPLE-19

5 g of the polymorphic Form-6 of Troglitazone, was heated to melt and the resulting transparent flake was crashed to give an yellowish white flue powder of the polymorphic Form-4 of Troglitazone in near quantitative yield. The polymorphic Form-4 of Troglitazone thus obtained was heated isothermally at a temperature in the range of 60° to 170° C. preferably 130° C. for a period in the range of 5 min. to 4 h, cooled to room temperature at a rate of 0.1° to 1° C./minute and crashed the resulting material to give the polymorphic Form-5 of Troglitazone in near quantitative yield.

Examples 20–21 illustrate the process for the preparation of the polymorphic Form-6 of Troglitazone

EXAMPLE-20

5 g of crude troglitazone obtained by the process as described in example-1 was dissolved in 25 ml of acetone and to this was added 100 ml of benzene. The clear solution thus obtained was rapidly cooled to 5° C. at the rate of 10° C./minute and allowed to stand at 5° C. for 12 h to yield 2.5 g of >99.0% pure polymorphic Form-6 of Troglitazone.

EXAMPLE-21

15.5 g of 5-[4-(6-hydroxy-2,5,7, 8-tetramethyl chroman-2-yl-methoxy) benzyl]-2-iminothiazolidine-4-one, prepared by the process as described in Example-1, was added to a mixture of 225 ml of acetic acid, 75 ml of conc. hydrochloric acid and 40 ml of water and the mixture was refluxed for 12 hrs. The reaction mixture was cooled to room temperature and 66.2 g of sodium bicarbonate was added and once the evolution of carbondioxide had ceased, the solvent was distilled off applying high vacuum. A 10:1 by volume mixture of benzene and ethyl acetate was added to the residue and the crude product was washed with a mixture of equal volumes of a saturated aq. sodium bicarbonate solution & water. The organic layer was dried over anhydrous sodium sulphate and the solvent was distilled off The resulting crude product was quickly eluted from a silica gel column with 50% ethylacetate-hexane to furnish 12.5 g of the required 5-{4-(6-hydroxy-2, 5, 7, 8-tetramethylchroman-2-yl-methoxy) benzyl) thiazolidine-2,4-dione (Troglitazone) with a HPLC purity of ~67–70%.

5 g of crude troglitazone as obtained above was dissolved in 25 ml of acetone and to this was added 100 ml of benzene. The clear solution thus obtained was rapidly cooled to 5° C. at the rate of 10° C./minute and allowed to stand at 5° C. for 12 h to yield 2.5 g of >99.0% pure polymorphic Form-6 of Troglitazone.

ADVANTAGES OF THE INVENTION

The polymorphic forms of Troglitazone are more active/bio-available.

Ease in formulation resulting in higher activity/bio-availability, in terms of lowering plasma blood sugar and plasma triglycerides.

We claim:

1. A polymorphic form 1 of Troglitazone having the formula

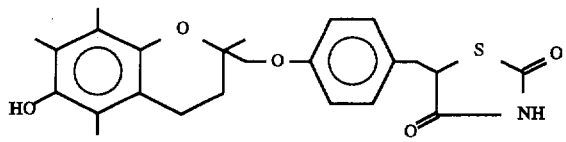

characterized by the data:

DSC: Endotherm at 179.3° C. (onset at 169.3° C.);

X-ray powder diffraction (2θ): 5.56, 11.10, 11.66, 15.72, 16.62, 17.62, 18.24, 19.70, 21.20, 21.42, 23.40, 23.70; and Infrared absorption bands (cm$^{-1}$): 3442(w), 3218(w), 2921(w), 1748(m), 1686(s), 1610(w), 1582(w), 1513 (s), 1454(w), 1420(w), 1382(w), 1302(m), 1244(s), 1169(m), 1118(w), 1086(w), 1048(m), 931(w), 863(w), 827(w), 798(w), 720(w), 509(w) wherein w=weak, m=medium, and s=strong.

2. A polymorphic form 2 of Troglitazone having the formula

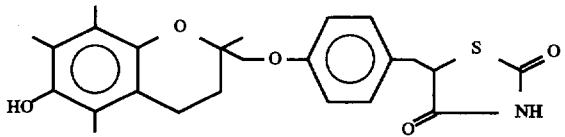

characterized by the data:

DSC: Endotherms at 110.1° C. (onset at 102.4° C.) and at 175.1° C. (onset at 155.9° C.);

X-ray powder diffraction (2θ): 5.42, 10.24, 10.72, 11.58, 11.72, 15.60, 17.56, 18.16, 19.48, 19.58, 19.68, 21.44, 22.20, 23.28, 23.66, 24.14, 24.38; and Infrared absorption bands (cm$^{-1}$): 3506(w), 3187(w), 3061(w), 2931(w), 1751(m), 1688(s), 1610(w), 1583 (w), 1512(s), 1454(w), 1419(w), 1381(w), 1334(w), 1301(m), 1252(s), 1165(m), 1088(w), 1047(w), 932 (w), 828(w), 722(w), 511(w) wherein w=weak, m=medium, and s=strong.

3. A polymorphic form 3 of Troglitazone having the formula

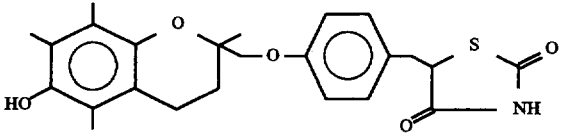

characterized by the data:

DSC: Endotherm at 185.8° C. (onset at 175.4° C.);

X-ray powder diffraction (2θ): 5.44, 11.74, 13.24, 15.62, 16.02, 17.56, 18.12, 19.65, 21.41, 23.00, 23.31, 23.65, 24.43, 26.517 and Infrared absorption bands (cm$^{-1}$): 3439(w), 3295(w), 2972(w), 2932(w) 1747(m), 1690(s), 1611(w), 1582 (w), 1512(s), 1453(m), 1384(w), 1302(m), 1245(s), 1221(s), 1169(s), 1143(w), 1119(w), 1089(w), 1049 (w), 931(w), 828(w), 722(w), 510(w) wherein w=weak, m=medium, and s=strong.

4. A polymorphic form 4 of Troglitazone having the formula

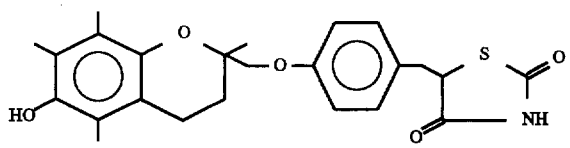

characterized by the data:

DSC: Endotherm at 56.6° C., exotherm at 110.4° C. (onset at 93.6° C.) and endotherm 177.1° C. (onset at 153.7° C.);

X-ray powder diffraction (2θ): No diffraction peaks due to its amorphous nature; and Infrared absorption bands (cm$^{-1}$): 3473(w), 3204(w), 3060(w), 2924(w) 1754(m), 1696(s), 1610(w), 1583 (w), 1512(s), 1457(m), 1420(w), 1378(w), 1333(m), 1301(m), 1243(s), 1162(m), 1115(w), 1085(w), 1041 (w), 928(w), 849(w), 827(w), 715(w), 664(w), 512(w) wherein w=weak, m=medium, and s=strong.

5. A polymorphic form 5 of Troglitazone having the formula

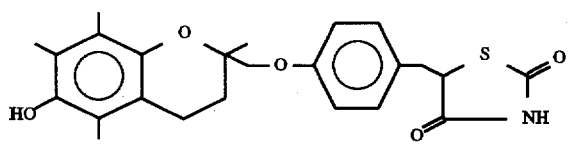

characterized by the data:

DSC: endotherm at 180.5° C. (onset at 157.9° C.);

X-ray powder diffraction (2θ): 5.60, 11.06, 11.62, 15.48, 15.78, 16.48, 18.12, 18.34, 21.06, 21.90, 23.34, 23.58; and Infrared absorption bands (cm$^{-1}$): 3462(w), 3211(w), 3060(w), 2921(w) 1303(m), 1244(s), 1168(m), 1117 (w), 1085(w), 1047(m), 929(w), 861(w), 825(w), 718 (w), 665(w), 564(w), 509(w) wherein w=weak, m=medium, and s=strong.

6. A polymorphic form 6 of Troglitazone having the formula

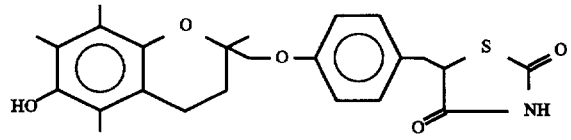

characterized by the data:

DSC: Endotherm at 105.4° C. (onset at 94.8° C.);

X-ray powder diffraction (2θ): 5.36, 8.54, 10.24, 10.70, 11.24, 12.48, 12.68, 15.58, 18.84, 19.48, 19.74, 20.58, 21.38, 21.56, 22.18; and Infrared absorption bands (cm$^{-1}$): 3634(w), 3514(w), 3176(w), 3060(w), 2930(w), 1753(m), 1686(s), 1610 (w), 1512(s), 1459(w), 1418(w), 1380(w), 1335(m), 1300(m), 1253(s), 1164(s), 1106(w), 1087(w), 1058 (w), 1048(w), 937(w), 828(m), 723(w), 673(w), 606 (w), 568(w), 515(w) wherein w=weak, m=medium, and s=strong.

7. A process for preparing the polymorphic form 1 of Troglitazone of claim 1 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent, or a mixture of polar organic solvents and heating the resulting solution with an organic non-polar solvent and (iv) cooling the resulting solution to room temperature at a rate of 0.1° to 1° C./minute over a period in the range of 24–72 h to produce the polymorphic Form 1 of Troglitazone.

8. A process for preparing the polymorphic form 2 of Troglitazone of claim 2 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of polar organic solvents and heating the resulting solution with an organic non-polar solvent and (iv) scratching the resulting solution, while cooling to a temperature between 0° to −20° C. at a rate of 2° to 10° C./minute over a period in the range of 10–30 min to precipitate the polymorphic form 2 of Troglitazone.

9. A process for preparing the polymorphic form 3 of Troglitazone of claim 3 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of polar organic solvents and heating the resulting solution with an organic non-polar solvent and (iv) scratching the resulting solution, while cooling to a temperature between 0° to −20° C. at a rate of 2° to 10° C./minute over a period in the range of 10–30 min to precipitate the polymorphic form 2 of Troglitazone (as claimed in claim 2), (v) dissolving the polymorphic form 2 of Troglitazone obtained in step (iv) in an organic polar solvent or a mixture of polar organic solvents and heating the resulting solution with an organic non-polar solvent and (vi) cooling the solution to room temperature at a rate of 0.1° to 1° C./minute over a period in the range of 24–72 h to crystallize polymorphic form 3 of Troglitazone.

10. A process for preparing the polymorphic form 4 of Troglitazone of claim 4 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of polar organic solvents and heating the resulting solution with an organic non-polar solvent, (iv) cooling the resulting solution to room temperature at a rate of 0.1° to 1° C./minute over a period in the range of 24–72 h to produce the polymorphic form 1 of Troglitazone (as claimed in claim 1), (v) filtering the polymorphic form 1 of Troglitazone and melting it by heating, (vi) cooling the melt to ambient temperature at a rate of 0.1° to 1° C./minute over a period in the range of 1–4 h to give a transparent material, (vii) grinding the transparent material to a fine powder to yield the polymorphic form 4 of Troglitazone.

11. A process for preparing the polymorphic form 4 of Troglitazone of claim 4 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of polar organic solvents and heating the resulting solution with an organic non-polar solvent, (iv) scratching the resulting solution while cooling to a temperature between 0° to −20° C. at a rate of 2° to 10° C./minute over a period in the range of 10–30 min to precipitate the polymorphic form 2 of Troglitazone (as claimed in claim 2), (v) filtering the polymorphic form 2 of Troglitazone and melting it by heating, (vi) cooling the melt of step (v) to ambient temperature at a rate of 0.1° to 1° C./minute over a period in the range of 1–4 h to give a transparent material, (vii) grinding the transparent material to a fine powder to yield the polymorphic form 4 of Troglitazone.

12. A process for preparing the polymorphic form 4 of Troglitazone of claim 4 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of organic polar solvents and heating the resulting solution with an organic non-polar solvent, (iv) scratching the resulting solution, while cooling to a temperature in the range of 0° to −20° C. at a rate of 2° to 10° C./minute over a period in the range of 10–30 min to precipitate the polymorphic form 2 of Troglitazone (as claimed in claim 2), (v) dissolving the polymorphic form 2 of Troglitazone obtained in step (iv), in an organic polar solvent or a mixture of polar organic solvents and heating the resulting solution with an organic non-polar solvent, (vi) cooling the solution to room temperature at a rate of 0.1° to 1° C./minute, over a period in the range of 24–72 h to crystallize polymorphic form 3 of Troglitazone, (vii) filtering the polymorphic form 3 of Troglitazone and melting it by heating, (viii) cooling the melt of step (vii) to ambient temperature at a rate of 0.1° to 1° C./minute, over a period in the range of 1–4 h to give a transparent material, (ix) grinding the transparent material to a powder to yield the polymorphic form 4 of Troglitazone.

13. A process for preparing the polymorphic form 5 of Troglitazone of claim 5 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of polar organic solvents and heating the resulting solution with an organic non-polar solvent, (iv) cooling the resulting solution to room temperature at a rate of 0.1° to 1° C./minute, over a period in the range of 24–72 h to produce polymorphic form 1 of Troglitazone (as claimed in claim 1), (v) filtering the polymorphic form 1 of Troglitazone and melting it by heating, (vi) cooling the melt of step (v) to ambient temperature at a rate in the range of 0.1° to 1° C./minute over a period of 1–4 h to give a transparent material, (vii) grinding the transparent material to a powder to yield polymorphic form 4 of Troglitazone (as claimed in claim 4), (viii) subjecting the polymorphic form 4 of Troglitazone so obtained in step (vii) to isothermal-heating in the range of 60° to 170° C. for a period in the range of 5 min. to 4 h, cooling to ambient temperature at a rate of 0.1° to 1° C./minute, over a period in the range of 1–4 h, followed by grinding to a powder to yield the polymorphic form 5 of Troglitazone.

14. A process for preparing polymorphic form 5 of Troglitazone of claim 5 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of polar organic solvents and heating the resulting solution with an organic non-polar solvent, (iv) scratching while cooling to a temperature in the range of 0° to −20° C. at a rate of 2° to 10° C./minute, over a period in the range of 10–30 min. to precipitate the polymorphic form 2 of Troglitazone (as claimed in claim 2), (v) filtering the polymorphic form 2 of Troglitazone and melting it by heating, (vi) cooling the melt of step (v) to ambient temperature at a rate in the range of 0.1° to 1° C./minute over a period of 1–4 h to give a transparent material, (vii) grinding the transparent material to a fine powder to yield the polymorphic form 4 of Troglitazone (as claimed in claim 4), (viii) subjecting the polymorphic form-4 of Troglitazone obtained in step (vii) to isothermal heating in the range of 60° to 170° C. for a period in the range of 5 min. to 4 h, cooling to ambient temperature at a rate of 0.1° to 1° C./minute, over a period in the range of 1–4 h, followed by grinding to a powder to yield the polymorphic form 5 of Troglitazone.

15. A process for preparing polymorphic form 5 of Troglitazone of claim 5 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of polar organic solvents and heating the resulting solution with an organic non-polar solvent, (iv) scratching the solution of step (iii) while cooling to a temperature in the range of 0° to −20° C. at a rate of 2° to 10° C./minute, over a period in the range of 10–30 min. to precipitate the polymorphic form 2 of Troglitazone (as claimed in claim 2), (v) dissolving the polymorphic form 2 of Troglitazone obtained in step (iv) in an organic polar solvent or a mixture of organic polar solvents and heating the resulting solution with an organic non-polar solvent, (vi) cooling the solution to room temperature at a rate of 0.1° to 1° C./minute, over a period in the range of 524–72 h to crystallize polymorphic form 3 of Troglitazone (as claimed in claim 3), (vii) filtering the polymorphic form 3 of Troglitazone and melting it by heating, (viii) cooling the melt of step (vii) to ambient temperature at a rate of 0.1° to 1° C./minute, over a period in the range of 1–4 h to give a transparent material, (ix) grinding the transparent material to a powder to yield polymorphic Form-4 of Troglitazone (as claimed in claim 4), (x) subjecting the polymorphic form 4 of Troglitazone obtained in step (ix) to isothermal heating in the range of 60° to 170° C. for a period in the range of 5 min. to 4 h, cooling to ambient temperature at a rate of 0.1° to 1° C./minute, over a period in the range of 1–4 h, followed by grinding to a powder to yield the polymorphic form 5 of Troglitazone.

16. A process for preparing polymorphic form 6 of Troglitazone of claim 6 which comprises:

(i) synthesizing Troglitazone in crude form, (ii) subjecting the crude Troglitazone obtained in step (i) to column chromatography to obtain a partially purified Troglitazone having HPLC purity in the range of 60–70%, (iii) dissolving the partially purified Troglitazone obtained in step (ii) in an organic polar solvent or a mixture of polar organic solvents and adding an organic non-polar solvent to the resulting solution and (iv) cooling the resulting solution to about 5° C. at a rate of 10° C./minute and maintaining the temperature at about 5° C. for a period of 10–16 h to produce the polymorphic form 6 of Troglitazone.

17. A process for preparing polymorphic form 4 of Troglitazone of claim 4 which comprises:

(i) melting a polymorphic form 5 of Troglitazone (as claimed in claim 5) by heating, (ii) cooling the melt of step (i) to ambient temperature at a rate of 0.1° to 1° C./minute, over a period in the range of 1–4 h to give a transparent material, and (iii) grinding the transparent material to a powder to yield the polymorphic form 4 of Troglitazone.

18. A process for preparing polymorphic form 4 of Troglitazone of claim 4 which comprises:

(i) melting a polymorphic form 6 of Troglitazone (as claimed in claim 6) by heating, (ii) cooling the melt of step (i) to ambient temperature at a rate of 0.1° to 1° C./minute, over a period in the range of 1–4 h to give a transparent material, and (iii) grinding the transparent material to a powder to yield the polymorphic form 4 of Troglitazone.

19. A process for preparing polymorphic form 5 of Troglitazone of claim 5 which comprises:

(i) melting polymorphic form 6 of Troglitazone (as claimed in claim 6) by heating, (ii) cooling the melt of step (i) to ambient temperature slowly at a rate of 0.1° to 1° C./minute, over a period in the range of 1–4 h to give a transparent material, (iii) grinding the transparent material to a powder to yield polymorphic form 4 of Troglitazone (as claimed in claim 4), (iv) subjecting the polymorphic form 4 of Troglitazone obtained in step (iii) to isothermal heating in the range of 60° to 170° C. for a period in the range of 5 min. to 4 h, cooling to ambient temperature slowly at a rate of 0.1° to 1° C./minute, over a period in the range of 1–4 h followed by grinding to a powder to yield polymorphic form 5 of Troglitazone.

20. A pharmaceutical composition comprising at least one of a polymorphic form of Troglitazone selected from the group consisting of polymorphic form 1 of Troglitazone, polymorphic form 2 of Troglitazone, polymorphic form 3 of Troglitazone, polymorphic form 4 of Troglitazone, polymorphic form 5 of Troglitazone and polymorphic form 6 of Troglitazone, as recited in any one of claims 1–6, and one or more pharmaceutically acceptable carriers, excipients, or diluents.

21. A method of treating diabetic ailments comprising administering to a patient in need thereof at least one of a polymorphic form of Troglitazone selected from the group consisting of polymorphic form 1 of Troglitazone, polymorphic form 2 of Troglitazone, polymorphic form 3 of Troglitazone, polymorphic form 4 of Troglitazone, polymorphic form 5 of Troglitazone, and polymorphic form 6 of Troglitazone, as recited in any one of claims 1–6.

* * * * *

UNITED STATES PATENT AND TRADEMARK OFFICE

CERTIFICATE OF CORRECTION

PATENT NO. : 5,700,820

DATED : December 23, 1997

INVENTOR(S) : Krishnamurthi VYAS, et al.

Page 1 of 2

It is certified that error appears in the above-identified patent and that said Letters Patent is hereby corrected as shown below:

In column 5, line 23, delete "22.32" and "24.06, 24.36, 26.26".

In column 5, lines 51 to 55, "5.40" should be -- 5.42 -- "10.70, 11.70, 12.18" should be -- 10.72, 11.58, 11.72 --, delete "12.44, 12.66, 13.20", delete "16.02, 16.50 --, "17.58" should be -- 17.56 --, "18.82, 19.62, 20.40, 20.64" should be -- 19.48, 19.58, 19.68 --, "22.22, 23.30, 23.68, 24.16, 24.44" should be -- 22.20, 23.28, 23.66, 24.14, 24.38 -- and delete "26.54, 27.82, 29.20, 31.48".

In column 6, line 18, delete "heating the resulting solution on steam bath and".

In column 6, lines 26 to 28, "5.45, 11.76" should be -- 5.44, 11.74 --, "15.63, 16.03, 17.58, 18.13, 19.66, 21.42, 23.37, 23.67, 24.45" should be -- 15.62, 16.02, 17.56, 18.12, 19.65, 21.41, 23.00, 23.31, 23.65, 24.43 --, and "26.53" should be -- 26.517 --.

UNITED STATES PATENT AND TRADEMARK OFFICE

CERTIFICATE OF CORRECTION

PATENT NO. : 5,700,820

DATED : December 23, 1997

INVENTOR(S) : Krishnamurthi VYAS, et al.

It is certified that error appears in the above-identified patent and that said Letters Patent is hereby corrected as shown below:

In column 7, lines 56 to 57, delete "heating the resulting solution preferably on steam bath and".

In column 8, lines 35 to 37, "5.56, 11.02, 11.62, 15.38, 15.80, 16.42, 18.08" should be -- 5.60, 11.06, 11.62, 15.48, 15.78, 16.48, 18.12 -- and "21.84, 22.14, 23.32" should be -- 21.90, 23.34, 23.58 --.

In column 9, lines 34 and 35, delete "heating the resulting solution preferably on a steam bath and".

In column 10, lines 8 to 12, before "8.54" insert -- 5.36 -- and delete "14.04, 14.70, 14.74, 15.00", "18.52", "20.24" and "23.20, 23.30, 23.62, 24.10, 25.16, 27.76, 27.86, 28.88, 28.92, 29.12, 31.02".

Signed and Sealed this

Eleventh Day of January, 2000

Attest:

Q. TODD DICKINSON

*Attesting Officer*   *Acting Commissioner of Patents and Trademarks*